(12) United States Patent
Ding et al.

(10) Patent No.: US 11,819,294 B2
(45) Date of Patent: *Nov. 21, 2023

(54) SYSTEMS AND METHODS FOR FIBER OPTIC TRACKING

(71) Applicant: MAKO Surgical Corp., Weston, FL (US)

(72) Inventors: Jienan Ding, Weston, FL (US); Joseph J. Bos, Kalamazoo, MI (US); Tim Perez, Plantation, FL (US); Min Wu, Weston, FL (US); Saul Najera, Boca Raton, FL (US); Robert A. Brindley, Delton, MI (US)

(73) Assignee: MAKO Surgical Corp., Weston, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/943,314

(22) Filed: Sep. 13, 2022

(65) Prior Publication Data

US 2023/0000569 A1    Jan. 5, 2023

Related U.S. Application Data

(63) Continuation of application No. 16/712,432, filed on Dec. 12, 2019, now Pat. No. 11,478,307.

(Continued)

(51) Int. Cl.
*A61B 34/20* (2016.01)
*A61B 17/70* (2006.01)
(Continued)

(52) U.S. Cl.
CPC .......... *A61B 34/20* (2016.02); *A61B 17/7074* (2013.01); *A61B 2017/00867* (2013.01);
(Continued)

(58) Field of Classification Search
CPC ...... A61B 34/10; A61B 34/20; A61B 17/7074
See application file for complete search history.

(56) References Cited

U.S. PATENT DOCUMENTS

| | | | |
|---|---|---|---|
| 7,720,322 B2 | 5/2010 | Prisco | |
| 8,285,363 B2 | 10/2012 | Malackowski et al. | |

(Continued)

FOREIGN PATENT DOCUMENTS

| | | |
|---|---|---|
| EP | 3 037 056 | 6/2016 |
| WO | WO-2011/153126 A2 | 12/2011 |
| WO | WO-2015/038740 A1 | 3/2015 |

OTHER PUBLICATIONS

International Search Report and Written Opinion for International Application No. PCT/US2019/066031, dated Apr. 8, 2020, 20 pages.

(Continued)

*Primary Examiner* — Si Ming Ku
(74) *Attorney, Agent, or Firm* — FOLEY & LARDNER LLP

(57) ABSTRACT

A fiber optic tracking sensor includes an outer tube, a plurality of optical fibers within the outer tube and including a central optical fiber and a plurality of additional optical fibers, and one or more structural members within the outer tube and configured to provide a spacing between the plurality of optical fibers such that the central optical fiber is positioned along a central longitudinal axis of the outer tube and the plurality of additional optical fibers are spaced apart from one another and from the central optical fiber.

16 Claims, 12 Drawing Sheets

Related U.S. Application Data

(60) Provisional application No. 62/781,570, filed on Dec. 18, 2018.

(51) Int. Cl.
  *A61B 90/00* (2016.01)
  *A61B 17/00* (2006.01)
  *A61B 17/56* (2006.01)

(52) U.S. Cl.
  CPC ............... *A61B 2017/00871* (2013.01); *A61B 2017/564* (2013.01); *A61B 2034/2061* (2016.02); *A61B 2090/363* (2016.02); *A61B 2562/0266* (2013.01)

(56) References Cited

U.S. PATENT DOCUMENTS

| | | |
|---|---|---|
| 8,400,620 B2 | 3/2013 | Froggatt et al. |
| 8,560,083 B2 | 10/2013 | Janik et al. |
| 2007/0253617 A1 | 11/2007 | Arata et al. |
| 2011/0125165 A1* | 5/2011 | Simaan .................. A61F 9/007 29/428 |
| 2011/0230894 A1 | 9/2011 | Simaan et al. |
| 2015/0190123 A1* | 7/2015 | Park .................. A61B 10/0266 600/567 |
| 2016/0166341 A1 | 6/2016 | Iordachita et al. |
| 2016/0206384 A1 | 7/2016 | Dimaio et al. |
| 2016/0266005 A1 | 9/2016 | Bos |
| 2016/0374770 A1 | 12/2016 | Janik et al. |
| 2018/0014891 A1 | 1/2018 | Krebs et al. |
| 2018/0161075 A1 | 6/2018 | Neo et al. |
| 2019/0090966 A1 | 3/2019 | Kang et al. |

OTHER PUBLICATIONS

Roesthuis et al., On using an Array of Fiber Bragg Grating Sensors for Closed-Loop Control of Flexible Minimally Invasive Surgical Instruments, IEEE/RSJ International Conference on Intelligent Robots and Systems (IROS), Nov. 3-7, 2013, 7 pages.

* cited by examiner

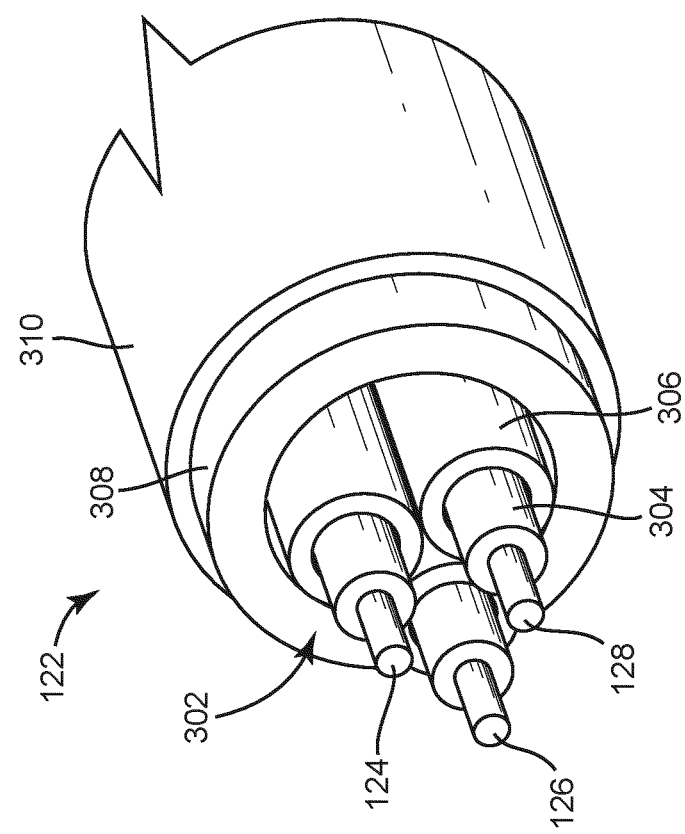
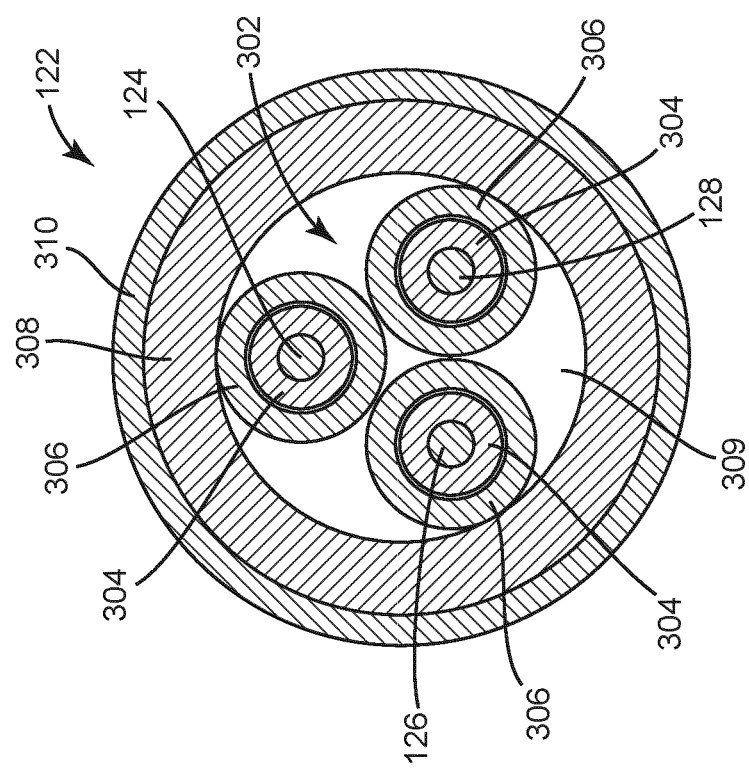

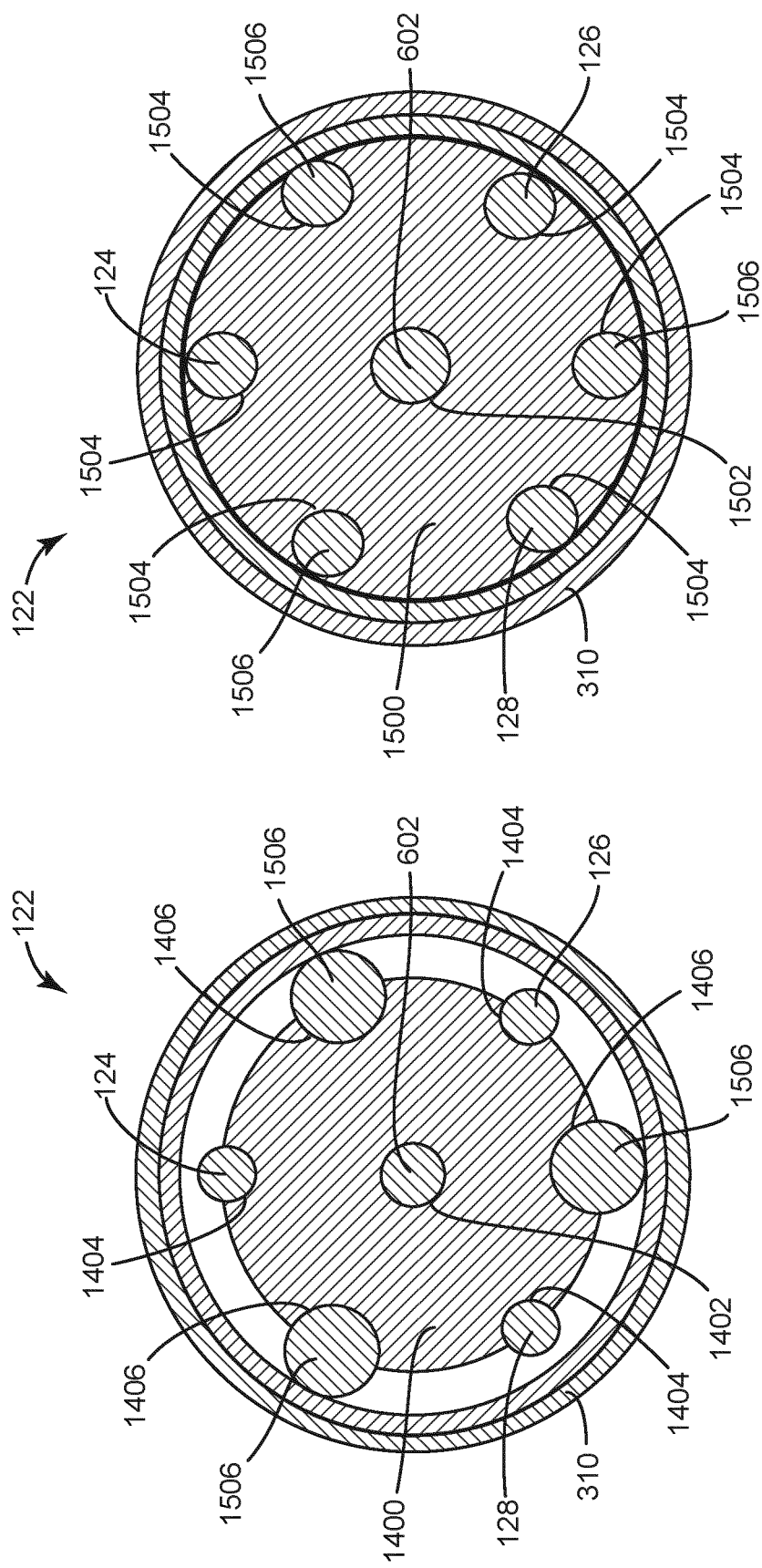

SYSTEMS AND METHODS FOR FIBER OPTIC TRACKING

CROSS-REFERENCE TO RELATED APPLICATIONS

This application is a continuation of U.S. patent application Ser. No. 16/712,432, filed Dec. 12, 2019, which claims the benefit of and priority to U.S. Provisional Application No. 62/781,570, filed Dec. 18, 2018. The entire disclosures of the above-referenced applications are incorporated by reference herein.

BACKGROUND

The present disclosure relates generally to the field of fiber optic tracking, and more particularly to a fiber optic tracking system for a surgical procedure.

Computer-assisted surgical systems have been developed to assist surgeons in performing precise surgical tasks. These systems generally rely on accurate information regarding the positions of a patient's anatomical features and surgical tools to provide surgical assistance, for example in the form of navigational assistance, robotic automation, or force feedback. To provide this position information, several varieties of tracking systems have been developed.

In some tracking systems, optical fibers are used to track objects in space. The optical fibers typically used in these systems include a number of sensing sections along their length known as fiber Bragg gratings. A fiber Bragg grating reflects a certain wavelength of light depending in part upon the strain experienced by the optical fiber at the sensing section. By analyzing the reflected wavelengths from multiple gratings, a three-dimensional model of the shape of the optical fiber may be generated. However, conventional fiber optic tracking systems suffer from a number of limitations. The measurement resolution of fiber optic tracking system is limited by the geometry of the hardware, and conventional hardware designs often do not provide sufficient resolution or accuracy for use in computer-assisted surgical systems. Conventional fiber optic tracking systems are also susceptible to errors caused by twisting of the optical fiber and internal friction between the optical fiber and a tube or casing used to protect the fiber, both of which affect the stress on the optical fiber and thus the wavelengths reflected by the fiber Bragg gratings.

Conventionally, surgical tracking systems are best suited to tracking the position of a single anatomical feature relative to a surgical tool, navigational pointer, etc. Thus, conventional tracking systems may be difficult, impractical, and/or overly invasive to implement when a surgical procedure demands the tracking of multiple anatomical features in a limited amount of space. For example, in a spinal surgery which would benefit from the assistance of a computer-assisted surgical system, the relative positions of the vertebrae may shift by more than two degrees and greater than two millimeters due to patient breathing and the effects of surgical activity (e.g., surgical exposure, discectomy, endplate preparation, decompression, hardware implantation, etc.). If only one spinal segment is tracked in a multi-level procedure, errors in the calculated positions of the other spinal segments resulting from these shifts may be great enough to result in serious damage to critical neurologic structures. Thus, a tracking system well-suited for tracking multiple objects, such as multiple anatomical features, multiple spinal segments, and/or multiple surgical tools or objects, is needed.

SUMMARY

One implementation of the present disclosure is a fiber optic tracking sensor. The fiber optic tracking sensor includes at least three optical fibers. Each optical fiber includes a plurality of fiber optic sensors positioned along a length of a sensing portion of the sensor and a shape-memory member coupled to the at least three optical fibers and providing support to the sensor. The at least three optical fibers are arranged in a spaced apart relationship, and each optical fiber is offset from a central longitudinal axis of the sensor.

In some embodiments, the fiber optic sensors include one or more of fiber Bragg gratings or Raleigh scattering, and the optical fiber includes one or more of standard telecommunications fiber, microstructured fiber, or hollow-core fiber. In some embodiments, the spaced apart relationship is an equilateral triangle.

In some embodiments, each optical fiber is surrounded by one of the plurality of tubes and wherein the tube surrounding each optical fiber is in contact with the tubes of the other two or more optical fibers forming a fiber core. The thicknesses of the tubes provides the spaced-apart relationship between the optical fibers and the offset from the central longitudinal axis of the tracking sensor. The fiber optic sensor may also include a sleeve positioned around the fiber core and between the fiber core and an outer tube. The sleeve may be made of one or more of a low-friction material or a thermally-insulating material.

In some embodiments, the fiber optic tracking sensor may also include a central optical fiber. The central optical fiber is surrounded by an inner tube. The inner tube is surrounded by the shape-memory member. The shape-memory member includes at least three indentations forming a channel between the inner tube and the shape-memory member for the at least three optical fibers.

In some embodiments, the shape-memory member includes a central wire. The fiber optic tracking sensor may include a sleeve surrounding the central wire and an outer tube surrounding the sleeve. The fiber optic tracking sensor may include a slotted tube between the central wire and the low friction sleeve, with the at least three optical fibers positioned in slots of the slotted tube. The central wire may include at least three indentations forming a channel between the central wire and the sleeve. The at least three optical fibers may be positioned at the at least three indentations.

In some embodiments, the shape-memory member is made of one or more of a shape memory alloy, nitinol, polyether ether ketone, polytetrafluoroethylene, glass, metal, plastic, aluminum, or steel.

Another implementation of the present disclosure is a computer-assisted surgical system. The computer-assisted surgical system includes a computing system including a processing circuit and a tracking circuit and a fiber optic tracking system in communication with the computing system to provide tracking data to the computing system. The fiber optic tracking system includes an interrogator and a sensor. The sensor includes at least three optical fibers, each optical fiber comprising a plurality of fiber optic sensors along a length of a sensing portion of the sensor. The at least three optical fibers are arranged in a spaced apart relationship, each optical fiber offset from a central longitudinal axis of the sensor. The offset of the at least three optical fibers from the central longitudinal axis of the sensor increases the resolution of tracking data for the surgical system.

In some embodiments, the computer-assisted surgical system includes a first attachment device for coupling the sensor to a first anatomical feature of a patient for tracking the first anatomical feature using the fiber optic tracking system and a second attachment device for coupling the sensor to a second anatomical feature of the patient for tracking the second anatomical feature using the fiber optic tracking system.

In some embodiments, the computer-assisted surgical system includes an optical tracking system for registering the sensor with the first anatomical feature and the second anatomical feature so that tracking data from the sensor provides information on a position of the first anatomical feature and a position of the second anatomical feature. The computer-assisted surgical system may include a fiducial on the first attachment device.

Another implementation of the present disclosure is a method of tracking anatomy of a patient using a fiber optic tracking system. The method includes coupling a fiber optic tracking sensor to the anatomy of the patient. The fiber optic tracking sensor includes at least three optical fibers, with each optical fiber including a plurality of fiber optic sensors along a length of a sensing portion of the sensor. The at least three optical fibers are arranged in a spaced apart relationship. Each optical fiber is offset from a central longitudinal axis of the sensor. The method includes registering the fiber optic tracking sensor with the anatomy to define the relationship between the tracking sensor and the anatomy. The method also includes transmitting light from an interrogator through the tracking sensor and receiving, at the transmitter, reflections from the sensor which provide strain data for the tracking sensor, transmitting the strain data to a tracking circuit to determine the shape of the tracking sensor, and determining a pose of the anatomy based on the shape of the tracking sensor.

In some embodiments, coupling the tracking sensor to the anatomy comprises coupling one or more attachment devices to the anatomy and coupling the tracking sensor to the one or more attachment devices. Each fiber optic sensor may be configured to reflect a particular wavelength of light back to the interrogator based on stress on the optical fiber at a location of the fiber optic sensor.

In some embodiments, registering the tracking sensor comprises using a probe of an optical tracking system to identify one or more points on the anatomy and one or more points on the sensor. In some embodiments, the method includes tracking one or more vertebrae of the patient's spine.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE DRAWINGS

The accompanying drawings, which are incorporated in and constitute a part of this specification, illustrate several embodiments that, together with the description, serve to explain the principles and features of the present disclosure.

FIG. 3 is a cross-sectional view of the sensor of the fiber optic tracking system of FIG. 1, according to an exemplary embodiment.

FIG. 4 is a perspective view of the sensor of FIG. 3, according to an exemplary embodiment.

FIG. 14 is a cross-sectional view of a sixth alternative embodiment of the sensor of the fiber optic tracking system of FIG. 1.

FIG. 15 is a cross-sectional view of a seventh alternative embodiment of the sensor of the fiber optic tracking system of FIG. 1.

DETAILED DESCRIPTION

Reference will now be made in detail to exemplary embodiments of the present disclosure, examples of which are illustrated in the accompanying drawings.

Referring generally to the figures, systems and methods for fiber optic tracking are shown. More particularly, a computer-assisted surgical system is shown with a fiber optic tracking system that includes an improved fiber optic sensor. According to various embodiments, the fiber optic sensor includes at least three optical fibers arranged with one or more shape-memory members (e.g., tubes, rods, wires, etc.) and one or more thermally-insulating low-friction sleeves (e.g., made of polytetrafluoroethylene (PTFE)) to provide improved measurement resolution and accuracy, minimize twisting- and friction-based errors, and provide thermal insulation to minimize temperature-based errors. The one or more shape-memory members may be formed from any shape-memory material, for example a shape-memory alloy (e.g., nitinol), polyether ether ketone, PTFE, wrapped wire, and other materials including glass, metal (aluminum, steel), plastic, etc. The fiber optic tracking system is structured to simultaneously track the positions of multiple anatomical features, which may be particularly useful for tracking a series of vertebra in a spinal procedure, for example in a spine L4 and L5 fusion case or a discectomy. As such, the embodiments described herein relate to spinal anatomy and surgical procedures involving the spine. It should be understood that the systems and methods for fiber optic tracking described herein are also well suited for a variety of other surgical applications, for example in hip or knee replacement procedures, and/or for tracking other anatomical structures or bones, and that all such applications are within the spirit and scope of the present disclosure.

Figure 1:
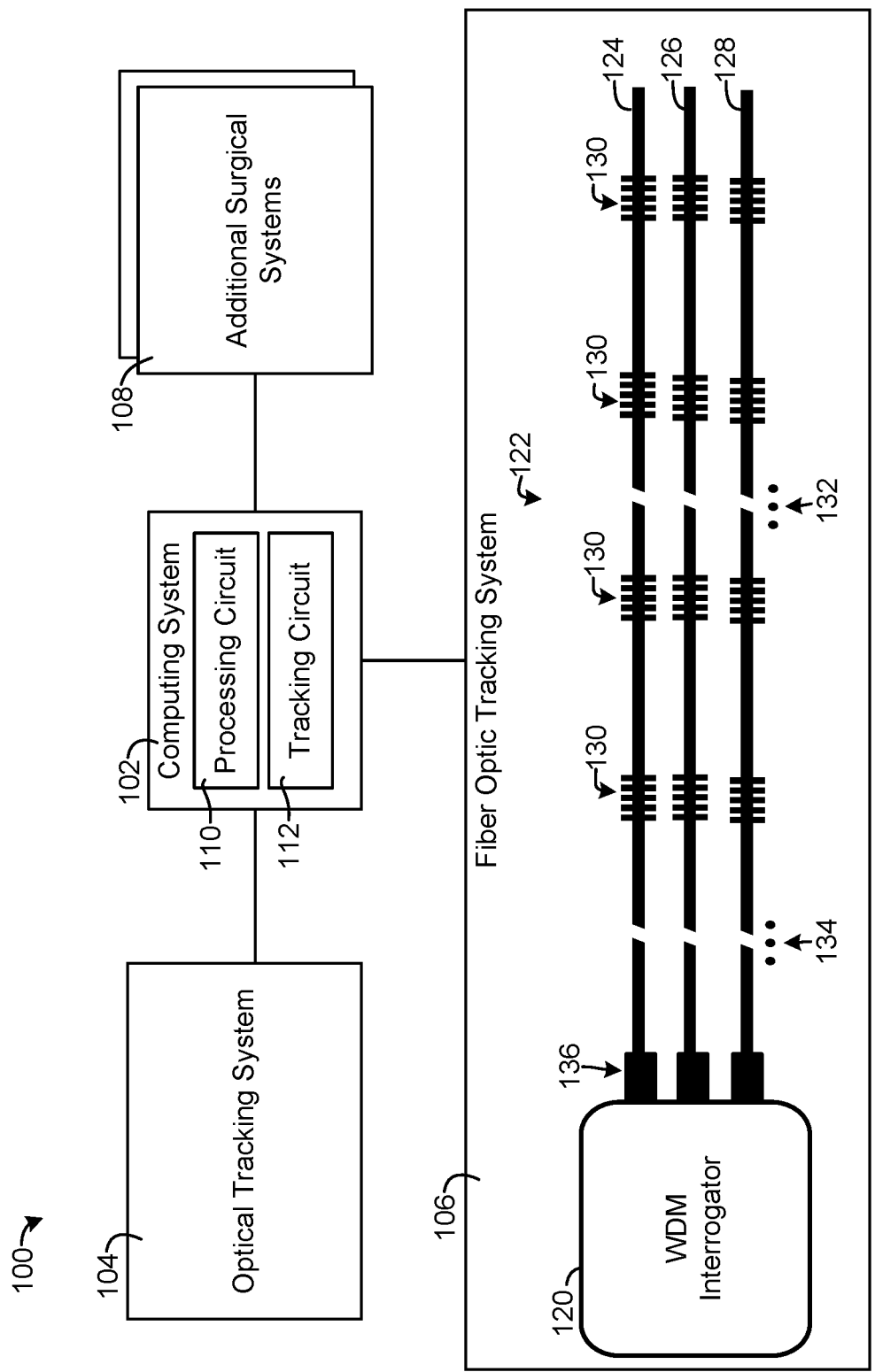
FIG. 1 is a block diagram of a computer-assisted surgical system with a fiber optic tracking system, according to an exemplary embodiment.

Referring to FIG. 1, a computer-assisted surgical system 100 is shown, according to an exemplary embodiment. The computer-assisted surgical system 100 includes a computing system 102 communicably and operably coupled to a fiber optic tracking system 106 and, optionally, an optical tracking system 104. In some embodiments, the computing system 102 is also communicably and operably coupled to one or more additional surgical systems 108.

The computing system 102 is configured to complete the computing and processing functions of the computer-assisted surgical system 100 described herein. The computing system 102 includes a processing circuit 110 and a tracking circuit 112. The processing circuit 110 includes one or more memory devices and a processor. The processor may be implemented as a general purpose processor, an application specific integrated circuit, one or more field programmable gate arrays, a digital signal processor, a group of processing components, or other suitable electronic processing components. The one or more memory devices (e.g., RAM, ROM, NVRAM, Flash Memory, hard disk storage, etc.) may store data and/or computer code for facilitating at least some of the various processes described herein. In this regard, the memory may include tangible, non-transient computer-readable media. The memory is communicably coupled to the processor and may store computer code for executing (by the processor) one or more processes described herein. When the processor executes instructions stored in the memory, the processor generally configures the computing system to complete such activities.

The tracking circuit 112 is configured to receive data from the optical tracking system 104 and, optionally, the fiber optic tracking system 106, and analyze that data to determine the positions of multiple anatomical features of a patient. Details of this analysis are described below with reference to FIG. 5. As shown, the tracking circuit 112 is a part of the computing system 102. In other embodiments, the tracking circuit 112 may be a separate, discrete component or be included with another component of the system 100 (e.g., included as part of the fiber optic tracking system 106 or the optical tracking system 104). It should be understood that the structure of the tracking circuit 112 is highly configurable. In the example shown, the tracking circuit 112 is structured as machine-readable media (e.g., non-transient computer readable medium that stores instructions that are executable by a process or processors to perform at least some of the processes described herein) that may be stored in and executed by the processing circuit 110. In alternative configurations, the tracking circuit 112 includes discrete processing components (e.g., processing and memory components with the same or similar configuration as described above for the processing circuit 110).

In general, the fiber optic tracking system 106 is configured to provide data that can be processed to determine the relative positions of anatomical features of a patient. The fiber optic tracking system 106, according to an exemplary embodiment, includes a wavelength division multiplexing (WDM) interrogator 120 and a sensor 122. The sensor 122 includes three optical fibers (fiber A 124, fiber B 126, and fiber C 128). Each optical fiber 124-128 includes a series of fiber optic sensors, such as fiber Bragg gratings (FBGs) 130, distributed substantially evenly along a sensing portion 132 of the sensor 122. In alternative embodiments, various other types of fiber optic sensors may be used, including fiber optic sensors based on Rayleigh scattering. The optical fibers 124-128 may include standard telecommunications fiber, microstructured fiber, or hollow-core fiber.

In various embodiments, various distributions and arrangements of the FBGs 130 along the optical fibers 124-128 are possible. For example, in the embodiment shown in FIG. 1, each optical fiber 124-128 includes a plurality of FBGs 130 (e.g., fifteen FBGs 130, twenty FBGs 130, etc.) spaced apart along the length of the sensing portion 132. As one illustrative example, in some embodiments each optical fiber 124-128 includes twenty FBGs 130 spaced approximately fifteen millimeters apart, so that the sensing portion 132 is approximately three hundred millimeters long (i.e., approximately one foot long). In other embodiments the FBGs 130 are positioned immediately adjacent to one another (i.e., zero spacing in between) and/or positioned to overlap one another. It should be understood that different numbers of FBGs 130, different spacing of the FBGs 130, and/or a different length of the sensing portion 132 are possible.

A greater number of FBGs 130 and tighter spacing between the FBGs 130 may provide for better accuracy of the fiber optic tracking system 106 while also requiring greater computational power to process the data provided by the fiber optic tracking system 106. An optimal number of FBGs 130 and/or spacing or overlap of FBGs 130 may therefore be determined by balancing improved accuracy versus increased computational expense associated with processing data from a greater number of FBGs 130. Accordingly, various embodiments consistent with the present disclosure include overlapping FBGs 130 and a spacing of FBGs 130 between zero and three centimeters.

In some embodiments, for example as shown in FIG. 1, the FBGs 130 in fiber A 124, fiber B 126, and fiber C 128 are substantially aligned across fibers 124-128, such that the FBGs 130 are grouped in triplets forming a sensing point corresponding to a particular position along the sensing portion 132. In other embodiments, the FBGs 130 are not or need not be substantially aligned across the fibers 124-128.

FBGs 130 are configured to reflect a particular wavelength of light while passing other wavelengths of light. The wavelength of light reflected by a particular FBG 130 shifts as the stress on the fiber at the position of the particular FBG 130 changes (i.e., a particular amount of wavelength shift from a reference wavelength corresponds to a particular amount of strain). In each fiber 124-128, each FBG 130 is tuned such that the possible reflected wavelengths are different for each FBG, facilitating differentiation between light reflected by each FBG 130 and ensuring that the wavelengths that can be reflected by a downstream FBG 130 reach that FBG 130.

The interrogator 120 provides broad spectrum light to the fibers 124-128, and receives light with the wavelengths reflected by the FBGs 130 in return. Because of the tuning of the FBGs 130, for each fiber 124-128 the return signal includes a differentiable wavelength corresponding to particular FBG 130. The interrogator 120 measures the wavelengths present in the return signal and provides the measured wavelengths to the computing system 102 for analysis. In alternative embodiments, a time division multiplexing interrogator is used that differentiates between the reflected light from each FBG based on the speed of light in in the fiber and the amount of time it takes for the reflected light to return to the interrogator.

The fiber optic tracking system 106 thereby provides a data point (e.g., wavelength) for each of the FBGs 130 that indicates the strain on the fiber at the location of the corresponding FBG 130. The data therefore includes measurements of the strain on fiber A 124, the strain on fiber B 126, and the strain on fiber C 128 at discrete locations along the sensing portion 132 of the sensor 122. As described in detail below, these data points can be used to generate a three-dimensional model of the sensor 122. A sample can be repeatedly taken over time, at some cases at a high frequency, to provide updated data that can be used to dynamically update the three-dimensional model.

Figure 2A:
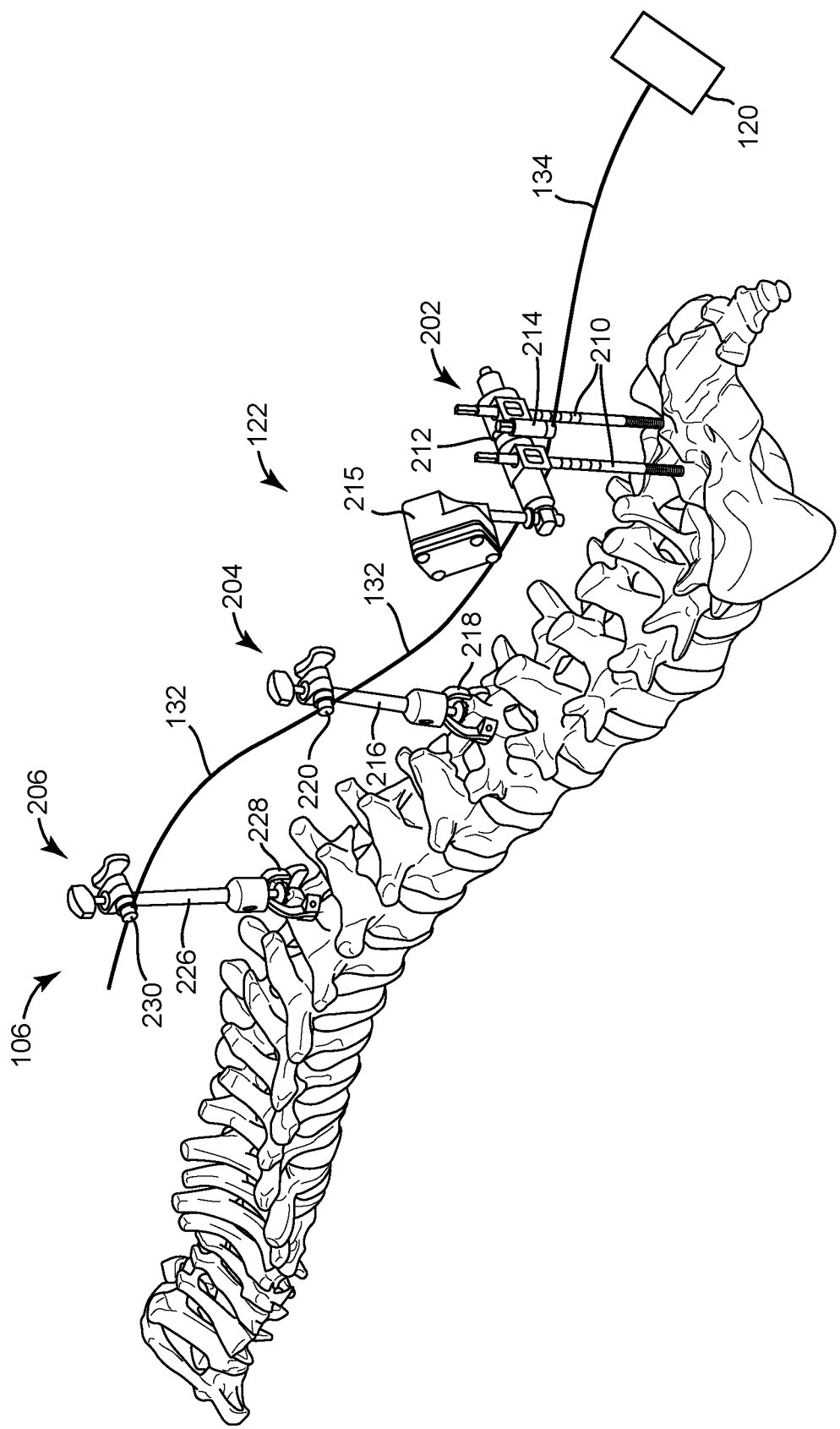
FIG. 2A is a perspective view of the fiber optic tracking system of FIG. 1 in an example application for a spinal procedure, according to an exemplary embodiment.
Figure 2B:
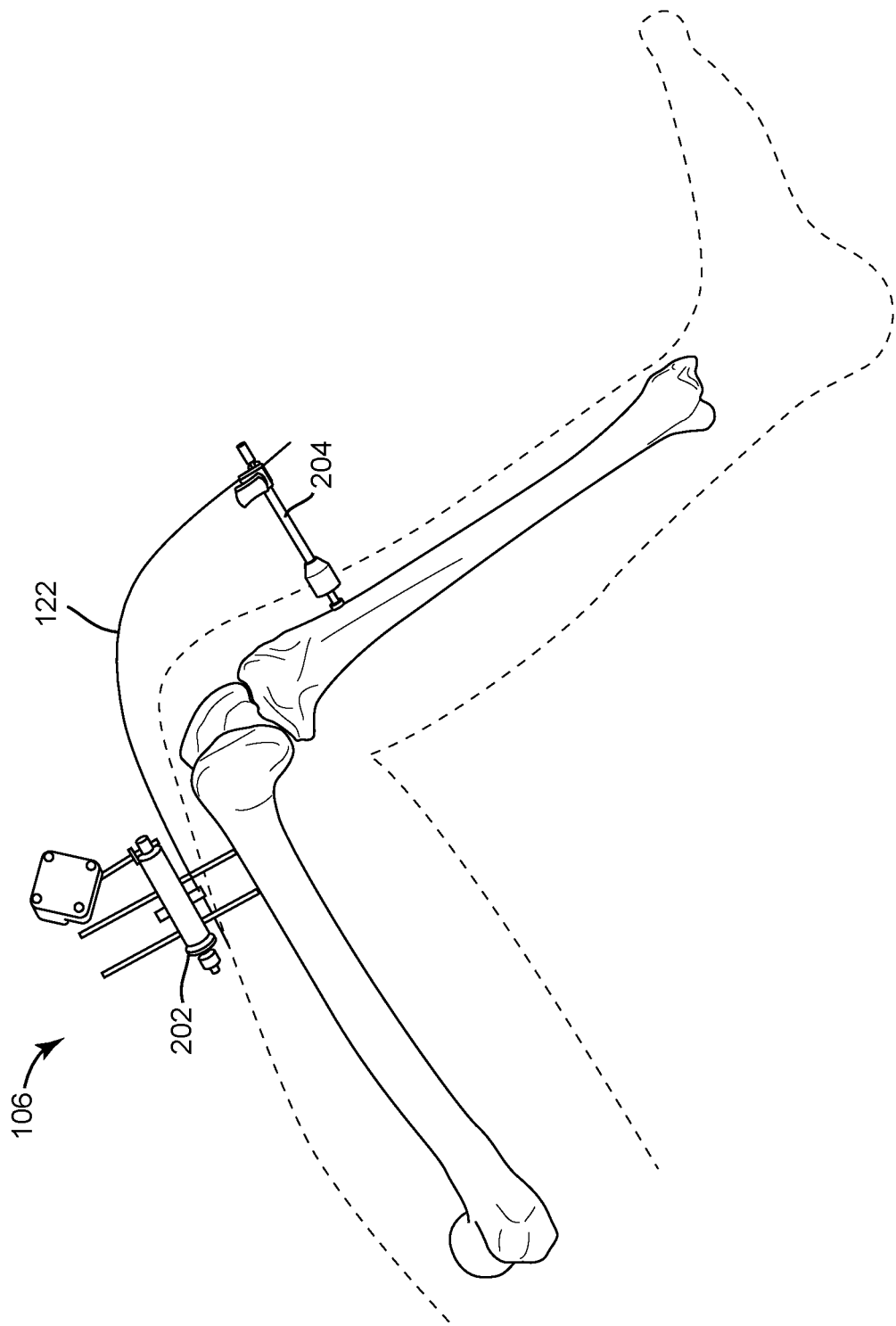
FIG. 2B is a perspective view of the fiber optic tracking system of FIG. 1 in an example application for a joint procedure, according to an exemplary embodiment.

A connecting portion 134 of the sensor 122 connects the sensing portion 132 to the interrogator 120, where each fiber 124-128 is received by a separate port 136. As shown in FIG. 1, the connecting portion 134 may be any suitable length, thereby allowing the sensing portion 132 to be positioned in a sterile surgical field while the interrogator 120 is positioned outside of the sterile surgical field. For example, as shown in FIGS. 2A-2B, the sensor 122 may be coupled to a plurality of anatomical features and the interrogator 120 is positioned away from the sensing area. The wavelength data collected by the interrogator 120 is then used by the computing system 102 to simultaneously track the positions of the plurality of anatomical features. In other examples, the sensor 122 may be coupled to multiple surgical tools (e.g., cutting guides, retractors, burrs, saws, etc.) to simultaneously track the positions of the surgical tools. In other examples, the sensor 122 is coupled to a probe to track the position of the probe. In still other examples, the sensor 122 may be coupled to one or more elements of additional surgical systems 108 (e.g., surgical robot, handheld robotic device, etc.) to track the positions of one or more elements of the additional surgical systems 108. For example, the sensor 122 may be coupled to various portions (e.g., joints, arms, end effectors, etc.) of a surgical robot to track the relative position of those various portions. In various other examples, the sensor 122 is coupled to a variety of one or more anatomical features, probes, surgical tools, robotic devices, etc. to simultaneously track a variety of types of objects.

The additional surgical systems 108 are systems, tools, accessories, etc. that provide assistance for the completion of a surgical procedure based, at least in part, on the tracking data provided by the fiber optic tracking system 106. In some embodiments, for example, the additional surgical systems 108 include a surgical robot. Based in part on data from the fiber optic tracking system 106, the surgical robot controls a surgical tool to carry out one or more surgical tasks. In some cases, the surgical robot is automatically actuated to complete one or more surgical tasks autonomously. In some cases, the surgical robot provides force feedback to a user to confine a surgical tool mounted on the surgical robot within a boundary defined relative to the tracked anatomy.

In some embodiments, the additional surgical systems 108 include a handheld robotic device. The handheld robotic device includes one or more actuators coupled to an end effector. The handheld robotic device is configured to control an end effector (e.g., a surgical too) in six degrees of freedom based on the position of the handheld robotic device, for example the handheld robotic device relative to one or more anatomical features of a patient and/or relative to a virtual control object generated by the computing system 102. The handheld robotic device thereby facilitates the completion of a surgical task using the end effector. In some cases, the handheld robotic device may be coupled to the sensor 122 and tracked by the fiber optic tracking system 106.

Another example of an additional surgical system 108 that may be included in system 100 is a navigation system including a pointer and a display screen. The pointer (e.g., a probe) includes an optical tracker that can be tracked by the optical tracking system 104 and/or the fiber optic tracking system 106. The display screen may display a representation of the pointer and a representation of the patient's anatomy to assist a surgeon in navigating the surgical field (e.g., to help a surgeon determine where to make an incision, determine an orientation at which to insert an implant or other surgical hardware, and/or to track surgical tools, etc.). The display may show the results of pre-operative or intra-operative imaging (e.g., CT, MRI, ultrasound), registered to the patient's anatomy using the optical tracking system 104. In addition to registering the patient's anatomy, the intra-operative imaging can also register the shape of the fiber to improve the intraoperative tracking. Many varieties and combinations of additional surgical systems 108 that provide surgical assistance based on the improved tracking capabilities of the computer-assisted surgical system 100 may be included with the computer-assisted surgical system 100.

The optical tracking system 104 is configured to facilitate a registration process for establishing a relationship between the sensor 122 and the patient's anatomy. In some embodiments, the optical tracking system 104 is also configured to register and track one or more components of the addition surgical system(s) 108 relative to the sensor 122 and the patient's anatomy. Accordingly, in the embodiment shown herein, the optical tracking system 104 includes fiducials that may be placed on various components of system 100, a probe including one or more fiducials, and an optical tracker configured to detect the three-dimensional position of the fiducials. The probe may be touched to various points along the sensor 122 and at corresponding points on the patient's anatomy to determine a geometric relationship between the sensor 122 and the anatomy, which will remain substantially constant as the anatomy shifts. The geometric relationship is then used by the computing system 102 in translating the wavelength data provided by the fiber optic tracking system 106 into a model of the three-dimensional positions of anatomical features. Fiducials coupled to a tool, pointer, robotic arm, etc. of the additional surgical system(s) 108 are tracked by the optical tracker relative to fiducials coupled to the sensor 122 (e.g., as shown in FIG. 2). The computing system 102 is configured to use this tracking data to control the additional surgical systems 108 to provide guidance, navigation, force feedback, and/or automated robotic control based on a determination of the relative positions of the component(s) of the additional surgical system(s) and the patient's anatomical features.

While an optical tracking system 104 is used for registration of the fiber optic tracking system 106 and other tracking functions in the embodiments shown herein, it should be understood that the fiber optic tracking system 106 may be used as a stand-alone tracking system, or may be used in combination with a variety of registration systems and methods. For example, in some embodiments, the fiber optic tracking system 106 is used in combination with an optical tracking system, a mechanical tracking system, an electromagnetic tracking system, and/or an inertial guidance system included in the computer-assisted surgical system 100 and used for registration of the sensor 122 and/or for tracking components of the additional surgical system(s) 108. In some embodiments, one or more additional fiber optic tracking systems 106 are included for use in registration of the sensor 122 and/or for tracking components of the additional surgical system(s) 108.

In some embodiments, the computer-assisted surgical system 100 includes a camera (i.e., video camera, RGB camera). In such embodiments, the camera may capture an image or series of images (i.e., video) of the sensor 122. The computing system 102 receives the image or images from the camera and uses a machine vision (i.e., image recognition) approach to identify the shape of the sensor 122 in the image or images. The shape of the sensor 122 identified based on the image(s) from the camera may then be used to facilitate registration of the sensor 122. The shape of the sensor 122 extracted from the image(s) from the camera may also compared to a shape of the sensor determined based on data from the fiber optic tracking system 106 to validate, calibrate, or otherwise improve the accuracy of the results of the fiber optic tracking system 106.

Referring now to FIGS. 2A-B, perspective views of the fiber optic tracking system 106 in use in two surgical applications are shown, according to exemplary embodiments. More particularly, FIG. 2A shows the fiber optic tracking system 106 in use for tracking three anatomical features along the spine of a patient (i.e., to facilitate a spinal procedure). FIG. 2B shows the fiber optic tracking system 106 in an example use to facilitate a procedure involving a patient's knee. The fiber optic tracking system 106 may also be used to track more or fewer anatomical features or objects (e.g., two, four, five, six, etc.) as needed for a particular procedure using a similar configuration as shown in FIGS. 2A-B. Furthermore, it should be understood that the fiber optic tracking system 106 can be used for tracking various bones for various other types of procedures, for example, for tracking the bones of a hip joint for a hip procedure, bones in a shoulder for a shoulder procedure, bones in a foot for a foot procedure, etc. In various other cases, the fiber optic tracking system 106 may be used to track soft tissue (e.g., ligaments, muscles, organs, etc.), surgical tools, or various other objects relating to various surgical procedures, including for open or minimally invasive surgical approaches.

FIG. 2A shows the sensor 122 coupled to attachment devices, shown as a base 202, a first bone clamp 204, and a second bone clamp 206. Various other attachment devices are contemplated by the present disclosure. The base 202 includes a pair of rods 210 coupled to the patient's sacrum, a crosspiece 212 joining the rods 210 and adjustably positionable along a height of the rods 210, a fiducial member 215 extending from the crosspiece 212 away from the patient's sacrum, and a sensor clamp 214 extending from the crosspiece 212 towards the sacrum between the rods 210. The sensor clamp 214 couples the sensor 122 to the base 202, and the position of the crosspiece 212 is adjustable along the rods 210 to allow the distance between the sensor 122 and the sacrum to be adjusted. The sensor 122 is thereby coupled to the patient's sacrum. The crosspiece 212 can be secured on the rods 210 to provide a fixed geometrical relationship between a point on the sensor 122 positioned in the sensor clamp 214 and the patient's sacrum. The fiducial member 215 has a known, fixed geometrical relationship to the sensor clamp 214 and thus to the point on the sensor 122 positioned in the sensor clamp 214. The fiducial member 215 includes fiducials trackable by, for example, the optical tracking system 104 shown in FIG. 1.

The first bone clamp 204 includes a rod 216 that extends from jaws 218 to sensor clamp 220. Jaws 218 securely couple the first bone clamp 204 to a first vertebra. Rod 216 extends away from the patient to the sensor clamp 220 and defines a fixed geometric relationship between the first vertebra and the sensor clamp 220. The sensor clamp 220 couples the sensor 122 to the first bone clamp 204, thus coupling the sensor 122 to the first vertebra and providing a fixed geometric relationship between a point on the sensor 122 and the first vertebra. The sensor clamp 220 may be rotatable relative to the rod 216 to allow the sensor 122 to pass through the sensor clamp 220 while minimizing any additional strain on the sensor 122 that could add errors to the measurements made by the fiber optic tracking system 106.

The second bone clamp 206 includes a rod 226 that extends from jaws 228 to sensor clamp 230. Jaws 228 securely couple the second bone clamp 206 to a second vertebra. Rod 226 extends away from the patient to the sensor clamp 230 and defines a fixed geometric relationship between the second vertebra and the sensor clamp 230. The sensor clamp 230 couples the sensor 122 to the second bone clamp 206, thus coupling the sensor 122 to the second vertebra and providing a fixed geometric relationship between a point on the sensor 122 and the second vertebra. The sensor clamp 230 may be rotatable relative to the rod 226 to allow the sensor 122 to pass through the sensor clamp 230 while minimizing any additional strain on the sensor 122 that could add errors to the measurements made by the fiber optic tracking system 106.

The sensor 122 runs from the base 202 to the first bone clamp 204 to the second bone clamp 206. The sensor clamps 214, 220, 230 are positioned along the sensing portion 132 of the sensor 122 (i.e., the section that includes the FBGs 130). The connecting portion 134 of the sensor 122 runs from the base 202 to the interrogator 120, which may be positioned outside of the sterile surgical field.

FIG. 2A shows an example application of the fiber optic tracking system 106 in an open spinal procedure. In various other applications and embodiments for spinal procedures, the base 202, the first bone clamp 204, and the second bone clamp 206 may be placed on various other bones (e.g., other vertebrae) than as in the example of FIG. 2A. Various other numbers of bone clamps may be included (one, three, four, five, etc.) to facilitate tracking of various numbers of bones. The example of FIG. 2A shows a posterior approach to the spine, while the fiber optic tracking system 106 may also be suitable for anterior and lateral approaches including with an open, minimally invasive, or percutaneous approach.

FIG. 2B shows an example application of the fiber optic tracking system 106 for a knee procedure (e.g., total knee arthroplasty, partial knee arthroplasty). The base 202 is coupled to the patient's femur, and the first bone clamp 204 is clamped onto the patient's tibia. The sensor 122 is coupled to the base 202 and the first bone clamp 204 and runs from the base 202 to the first bone clamp 204. The sensor 122 is secured with a fixed geometric relationship to the femur and a fixed geometric relationship to the tibia. The fiber optic tracking system 106 is thereby positioned to track the relative positions (location, orientation, etc.) of the femur and the tibia, for example to facilitate a knee arthroplasty procedure. Various other applications of the fiber optic tracking system 106 are contemplated by the present disclosure.

In some embodiments, the fiber optic tracking system 106 may be used in a minimally-invasive procedure. For example, surgical staples or other minimally-invasive mounting structures may be used in place of the base 202 and bone clamps 204, 206 to couple the sensor 122 to the anatomy or other tracked object. In other implementations, the sensor 122 may be inserted into the patient (e.g., into a patient's bone, skin, etc.). For example, the sensor 122 may be included in a flexible endoscope or other minimally-invasive tool or robotic device. The sensor 122 may provide percutaneous or subcutaneous tracking. In embodiments where the sensor 122 is inserted into the patient, intraoperative computed tomography may be used to facilitate registration.

Referring now to FIGS. 3 and 4, detailed views of the sensor 122 are shown, according to an exemplary embodiment. FIG. 3 shows a cross-sectional end view of the sensor 122 and FIG. 4 show a perspective view of the sensor 122. In general, the sensor 122 is structured to maintain a geometric relationship between fiber A 124, fiber B 126, and fiber C 128, protect the fibers 124-128 from damage, prevent twisting of the sensor 122, limit thermal response of the FBGs 130, and limit friction within the sensor 122. In preferred embodiments, the geometric relationship is a spaced apart relationship between the fibers, with each fiber offset from the central longitudinal axis of the sensor 122. In some embodiments, three fibers form an equilateral triangle.

Each fiber 124-128 is positioned within a casing 302, and may be adhered (e.g., glued, otherwise coupled) to the corresponding casing 302. In the embodiment of FIGS. 3 and 4, each casing 302 includes two concentric tubes (first tube 304 and second tube 306) with circular cross-sections. The first tube 304 has an inner radius substantially similar to the radius of each fiber 124-128 and an outer radius substantially similar to an inner radius of the second tube 306. The second tube 306 thereby fits snuggly around the first tube 304, and the first tube 304 fits snuggly around a fiber 124-128 (i.e., fiber A 124, fiber B 126, or fiber C 128). The first tube 304 and the second tube 306 are preferably made of nitinol, but may also be made of other suitable shape-memory materials (e.g. shape memory alloy, steel, aluminum).

The three second tubes 306 are positioned abutting one another, such that the casing 302 for each fiber (e.g., fiber A 124) abuts the casings 302 for both of the other fibers (e.g., fiber B 126 and fiber C 128). The casings 302 have substantially equal radii, and are positioned such that the fiber A 124, fiber B 126, and fiber C 128 form an equilateral triangle in the cross-sectional view of FIG. 3. In some embodiments, the casings 302 are adhered (e.g., glued, otherwise coupled) together in the geometric relationship shown in FIGS. 3-4.

A low-friction sleeve 308 encases the casings 302. The low-friction sleeve 308 is preferably made of polytetrafluoroethylene (PTFE) (e.g., Teflon) or other material that slides with low friction along the casings 302 and provides thermal insulation. The low-friction sleeve 308 minimizes friction as bending of the sensor 122 causes the casings 302 and the fibers 124-128 to shift slightly along the length of the sensor 122. The low-friction sleeve 308 thereby helps to minimize errors in the strain measurements of the FBGs 130 caused by friction. The low-friction sleeve 308 also provides thermal insulation for the fibers 124-128, minimizing the risk of errors that might otherwise be caused by temperature changes in the fibers 124-128. The low-friction sleeve 308 also allows for relative longitudinal rotation of the fibers 124-128 and the casings 302 to release torsional stress in the fibers 124-128, improving the accuracy of the sensor 122. The inner radius of the low-friction sleeve 308 is chosen such that each low-friction sleeve 308 abuts each casing 302 and surrounding air gaps 309 as shown in FIGS. 3 and 4.

An outer tube 310 surrounds the low-friction sleeve 308, the casings 302, and the fibers 124-128. The outer tube 310 provides an outer, circular structure to the sensor 122 that supports the geometric relationship between fibers 124-128 shown in FIGS. 3-4. The outer tube 310 fits snuggly around the low-friction sleeve 308. The outer tube 310 is preferably made of nitinol, although other suitable shape-memory materials may be possible. The diameter of the outer tube 310 is between one and two millimeters, in the embodiment shown.

Nitinol is a preferred material for the first tube 304, the second tube 306, and the outer tube 310 due to its high elasticity, allowing the sensor 122 to be bent into a wide range of geometries to follow a patient's anatomical features (e.g., to join the base 202, first bone clamp 204, and second bone clamp 206 of FIG. 2A across a variety of possible arrangements) while still providing support and protection for the fibers 124-128. Nitinol can be deformed up to 5% strain without damage, allowing the sensor 122 to be bent without damage. As another example, the outer tube 310 prevents non-path-based influences from altering the strain measured by the FBGs 130 by protecting the fibers 124-128 from pressure applied on the sensor 122 by the sensor clamps 214, 220, 230, patient tissue, or other object. The casings 302 (i.e., first tubes 304 and second tubes 306) similarly protect the fibers 124-128 from pressure or other influences potentially exerted by the neighboring casings 302 or the low-friction sleeve 308.

The offset between the fibers 124-128 in a sensor 122 designed according to the exemplary embodiments provides a significant increase in resolution as compared to conventional fiber optic approaches that use a single fiber. The maximal measurement resolution of an FBG sensor is determined by a scalar multiple of the offset between a neutral line along the center of the sensor and the FBGs. In a conventional, single fiber shape-sensing product, the offset is limited by the radius of the fiber and is therefore typically around 40-60 microns. In contrast, the sensor 122 includes three fibers 124-128 all separated from a neutral line that runs along a central axis 350 of the sensor 122, substantially increasing the offset between the FBGs 130 and the neutral line. In preferred embodiments, the offset in the sensor 122 is approximately 400 microns. In some embodiments, the offset of the sensor 122 is greater than 400 microns. The measurement resolution of the sensor 122 is therefore roughly tenfold better than the resolution of conventional optical fiber sensors.

Figure 5:
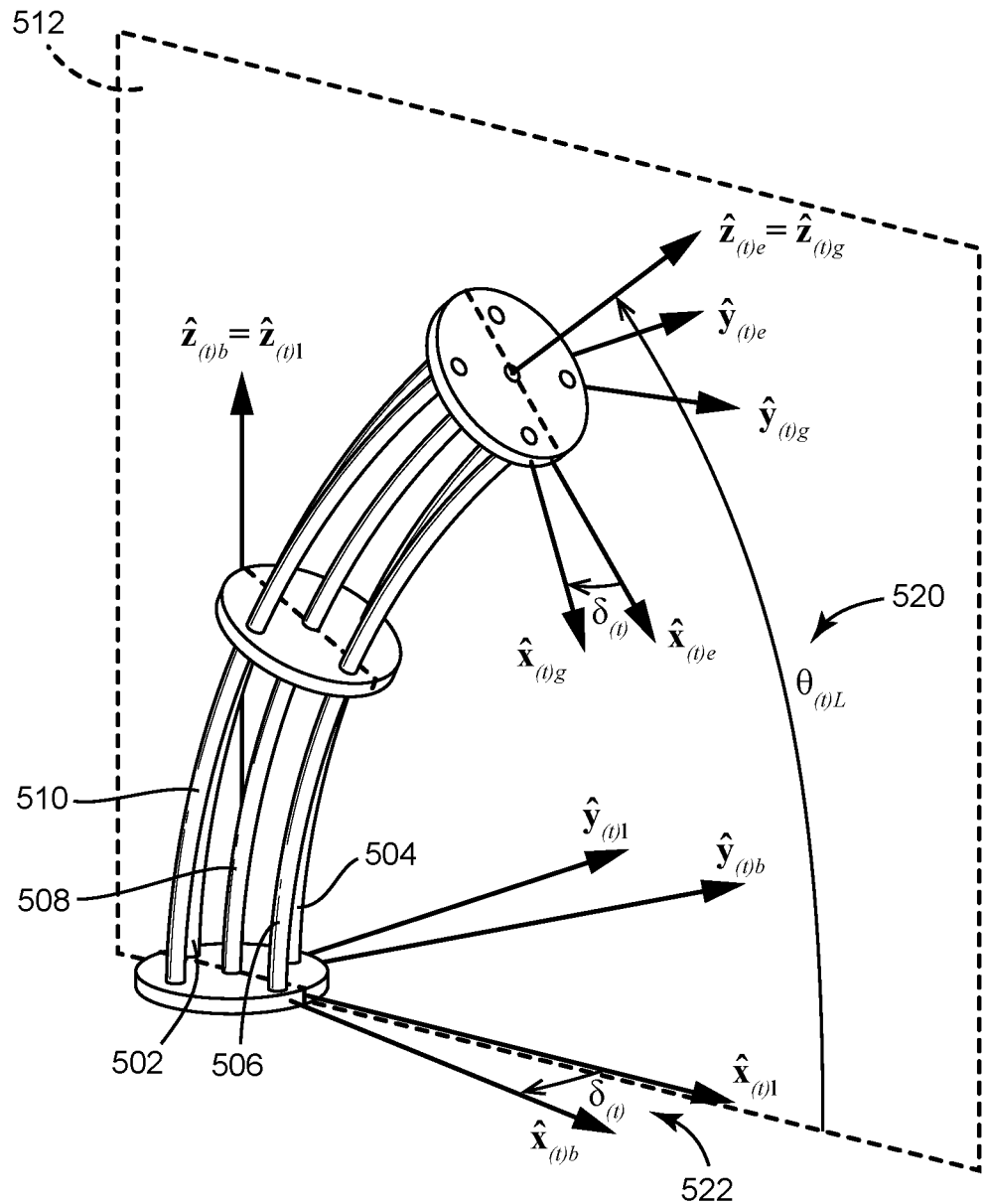
FIG. 5 is a diagram illustrating a kinematic model for use with the computer-assisted surgical system of FIG. 1, according to an exemplary embodiment.

Referring now to FIG. 5, a visualization 500 of the kinematic model used by the tracking circuit 112 in determining the shape of the sensor 122 is shown, according to an exemplary embodiment. FIG. 5 shows arc A 502 representing fiber A 124, arc B 504 representing fiber B 126, arc C 506 representing fiber C 128, and neutral arc 508 that represents a center line extending along a central axis of the outer tube 310 (i.e., a central axis of the sensor 122). FIG. 5 also shows an structural arc 510 corresponding to a secondary backbone of the sensor 122. Each arc 502-508 is given a partial circular shape over the segment shown in FIG. 5, i.e., each arc has a constant curvature such that it could be extended to form a complete circle. The arcs 502-506 represent a segment of the sensing portion 132 corresponding to a triplet of FBGs 130 (i.e., an FBG 130 on each of fiber A 124, fiber B 126, and fiber C 128).

The tracking circuit 112 receives wavelength data from the fiber optic tracking system 106 associated with the strains on each fiber 124-128 at a series of points (i.e., the positions of the FBGs) along the sensing portion 132 of the sensor 122. The strain on a fiber 124-128 at a particular point corresponds to a degree of curvature of that fiber 124-128 at that point. Additionally, the relative strain on the three fibers 124-128 at the particular point can be compared to determine a direction of the curvature at that point. That is, given the fixed geometric relationship of the fibers 124-128 in the sensor 122, differences between the strain (and thus the degrees of curvature) experienced by the individual fibers 124-128 indicate that the sensor 122 curves towards the fiber(s) 124-128 with the lower degrees of curvature.

For example, in the example of FIG. 5, arc A 502 has the lowest degree of curvature, arc B 504 has a slightly higher degree of curvature, and arc C 506 has the greatest degree of curvature of the three arcs 502-506. Given those relative degrees of curvature (i.e., relative strains) and the fixed geometric relationship between the three fibers 124-128 in the equilateral triangle of FIG. 3, only one direction of curvature of the sensor 122 (i.e., of the neutral arc 508) is possible, namely mostly towards fiber C 128 (i.e., arc C 506) and slightly towards fiber B 126 (i.e., arc B 504) as shown in FIG. 5.

Based on this analysis and as shown in FIG. 5, the path of the neutral arc 508 can be characterized by two parameters, namely a bending angle $\theta$ (shown by indicator 520) and a twisting angle $\delta$ (shown by indicator 522). The bending angle $\theta$ describes the degree to which the neutral arc 508 (and thus the sensor 122) is bent within a bend plane 512. The twisting angle $\delta$ characterizes the rotation about the z-axis of the bend plane relative to the preceding bend plane. To model the three-dimensional shape of the sensor 122, the tracking circuit 112 determines $\theta$ and $\delta$ for a plurality of segments of the sensor 122 and combines the resulting curves to generate an overall three-dimensional shape. Each portion may correspond to one triplet of FBGs 130.

In various embodiments, the tracking circuit 112 applies one or more of a variety of possible error corrections. In some embodiments, the tracking circuit 112 is configured to correct for misalignment of the FBGs 130 across the multiple fibers 124-128. In some embodiments, temperature is monitored across the multiple fibers 124-128 to determine a temperature differential amongst the fibers 124-128 at one or more locations along the fibers 124-128. The tracking circuit 112 may be configured to minimize errors created by such a temperature differential.

The modelled, three-dimensional shape of the sensor 122 allows the relative positions of any two or more points along the sensor 122 to be identified with sub-millimeter accuracy. In the example of FIG. 2A, for instance, the relative positions of the three sensor clamps 214, 220, 230 (i.e., the position of a point on sensor 122 at each sensor claim 114, 120, 130) can be determined.

The known geometric relationship (e.g., based on a registration process) between each sensor clamp 214, 220, 230 and a particular anatomical feature allows the tracking circuit 112 to determine the relative positions of those anatomical features. The fixed geometric relationship between the fiducial member 215 and the sensor clamp 214 allows the positions of the anatomical features to be determined relative to a reference coordinate system of the optical tracking system 104.

Components of the additional surgical system(s) 108 may also be tracked relative to that reference coordinate system, and can be controlled to provide navigation features, force feedback, automatic manipulation of tissue, etc. based on the positions of the anatomical features in that reference coordinate system as determined by the approach described above. The computer-assisted surgical system 100 thereby provides a hybrid tracking approach in which the fiber optic tracking system 106 is used to accurately pinpoint the positions of multiple anatomical features while the optical tracking system 104 is used to provide tracking of surgical tools, equipment, devices, etc. and registration to pre-operative or intra-operative imaging and planning. In various other embodiments, the surgical tools, equipment, devices, etc. are also tracked using a fiber optic tracking system 106.

Figure 6:
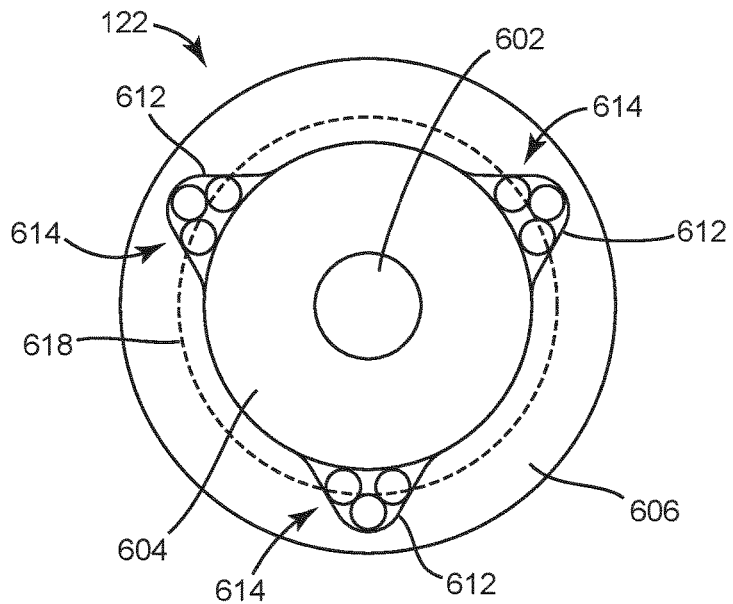
FIG. 6 is a cross-sectional view of a first alternative embodiment of the sensor of the fiber optic tracking system of FIG. 1.
Figure 7:
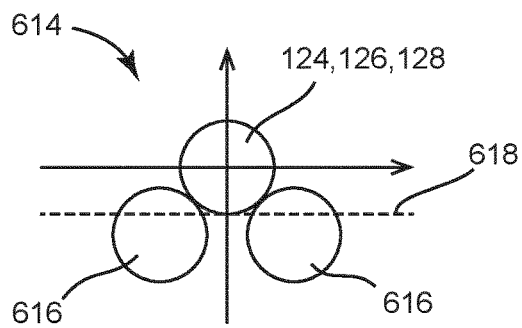
FIG. 7 is a cross-sectional view of a component of the sensor of FIG. 6, according to an exemplary embodiment.
Figure 8:
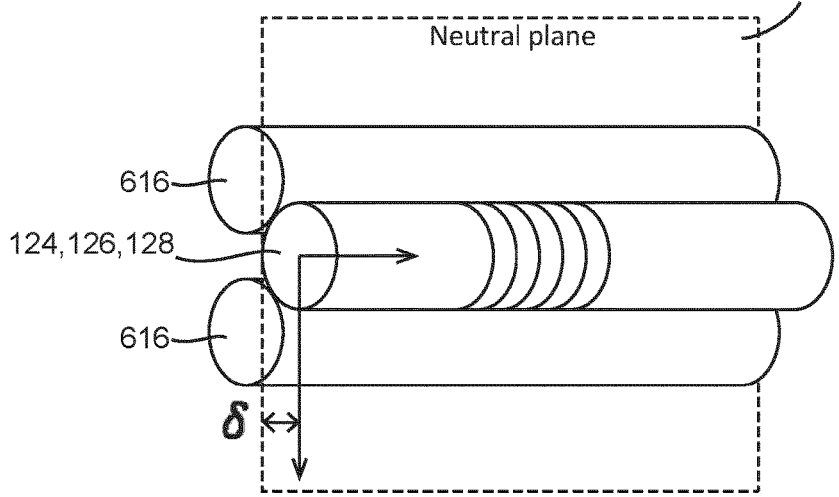
FIG. 8 is a perspective view of the component of the sensor of FIG. 6, according to an exemplary embodiment.

Referring now to FIGS. 6-18, a variety of alternative embodiments of the sensor 122 are shown. FIGS. 6-8 illustrate a first alternative embodiment of the sensor 122 that includes four optical fibers. As shown in FIG. 6, the sensor 122 includes a central optical fiber 602 in addition to fiber A 124, fiber B 126, and fiber C 128. The central optical fiber 602 is surrounded by an inner tube 604 and an outer tube 606. The inner tube 604 and the outer tube 606 are preferably made of nitinol or a material with similar characteristics. The outer tube 606 has an inner wall 608 that abuts the inner tube 604 around the circumference of the inner tube 604, with the exception of three indentations 610 in the outer tube 606 that define channels 612 between the inner tube 604 and the outer tube 606. Each channel 612 houses an assembly 614 that includes one fiber (i.e., fiber A 124, fiber B 126, or fiber C 128) and two wires 616. The outer tube 606 may be manufactured using an extrusion process to create the channels 612. The two wires 616 abut the inner tube 604. The wires 616 are preferably made of nitinol or a similar shape-memory material. In various embodiments, the wires 616 may have various degrees of stiffness or pliability. For example, in some embodiments the wires 616 are rigid. As another example, the wires 616 may be flexible.

FIGS. 7-8 illustrate the assembly 614 in detail from a cross-sectional end view and a perspective view, respectively. The assembly 614 includes a fiber 124-128 glued or otherwise coupled to two wires 616. Each wire 616 has roughly the same diameter as the fibers 124-128. The two wires 616 are positioned such that a line from the center of one wire 616 to the center of the fiber 124-128 to the center of the second wire 616 forms a substantially right angle (i.e., about 90 degrees). Other angles are also possible (e.g., 45 degrees, 60 degrees, 80 degrees, 120 degrees). In this arrangement, the assembly 614 has a neutral plane 618 offset from the center of the fiber, which may help increase the resolution of the sensor 122 as discussed above.

Figure 10:
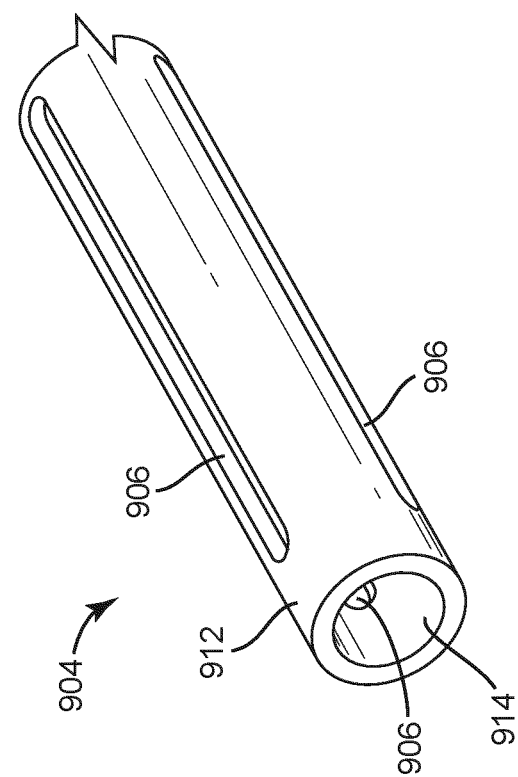
FIG. 10 is a perspective, partial view of a slotted tube used in the sensor of FIG. 9, according to an exemplary embodiment.
Figure 9:
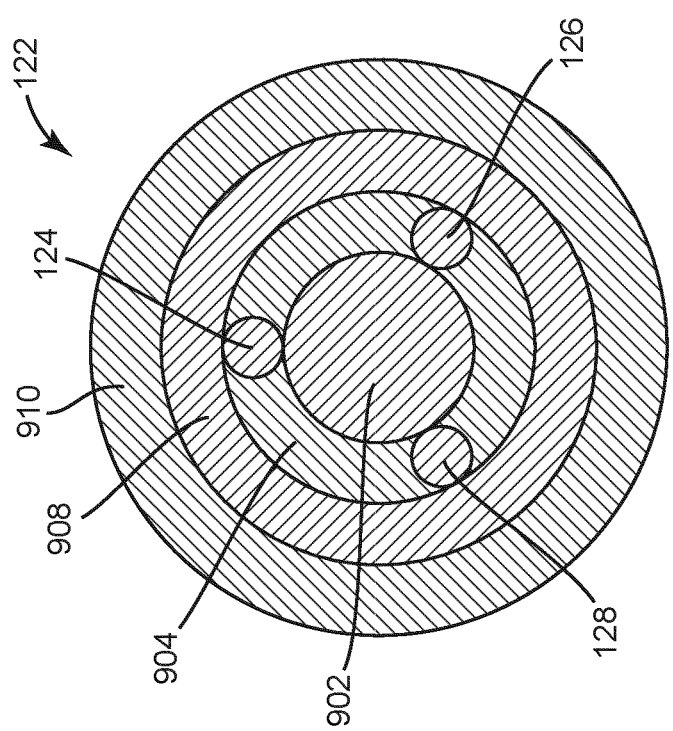
FIG. 9 is a cross-sectional view of a second alternative embodiment of the sensor of the fiber optic tracking system of FIG. 1.

Referring now to FIGS. 9-10, a second alternative embodiment of the sensor 122 is illustrated. As shown in FIG. 9, a central wire 902 is surrounded by a slotted tube 904, with an inner surface of the slotted tube 904 abutting the central wire 902. A perspective view of the slotted tube 904 is shown in FIG. 10. The slotted tube 904 includes three slots 906 positioned equidistant around the circumference of the slotted tube 904 and extending through the slotted tube 904. The slots 906 are sized substantially the same (e.g., slightly larger) than the fibers 124-128, and each slot 906 receives a fiber (i.e., fiber A 124, fiber B 126, or fiber C 128)

as shown in FIG. 9. The slots 906 may be created by laser machining with a high geometric accuracy, which may increase measuring accuracy of the sensor 122. The slots 906 may also be mechanically cut.

A low-friction sleeve 908 surrounds the slotted tube 904. The fibers 124-128 are held in the slots 906 between the central wire 902 and the low-friction sleeve 908, and are thus offset from the central axis (neutral line) of the sensor 122. The low-friction sleeve 908 also reduces friction, releases torsional stress (i.e., minimizes twisting), and provides thermal insulation for the sensor 122. Accordingly, the low-friction sleeve 908 is made of a low-friction, insulating material such as PTFE. An outer tube 910 surrounds the low-friction sleeve 908 to provide structure support and strength to the sensor 122. The central wire 902, the slotted tube 904, and the outer tube 910 are preferably made of nitinol or a material with similar characteristics.

In the embodiment shown in FIG. 10, the slots 906 are closed at the end 912 of the slotted tube 904. At the end 912, the fibers 124-128 may bend inward (i.e., towards the central wire 902) to allow the fibers 124-128 to extend through an opening 914 at the end 912 of the slotted tube 904. The central wire 902 may be tapered or slotted proximate the end 912 to allow this ingress/egress of the fibers 124-128. In some embodiments, the slotted tube 904 corresponds to the sensing portion 132 as shown in FIG. 1, while the end 912 separates the sensing portion 132 from the connecting portion 134. In alternative embodiments, the slots 906 are open at (e.g., extend through) the end 912 to allow the fibers 124-128 to enter the slots 906. In other embodiments, the slots 906 are open at both ends of the slotted tube 904, such that the slotted tube 904 includes three separate curved sections held together by the low-friction sleeve 908 and the outer tube 910.

Figure 11:
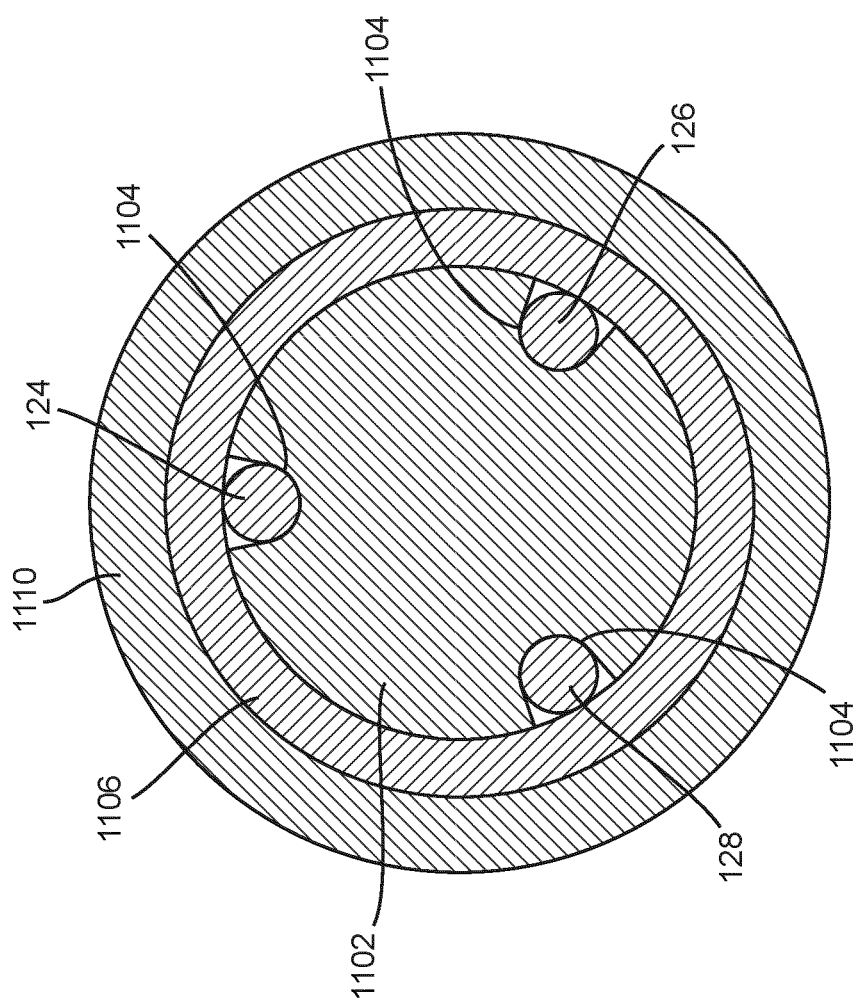
FIG. 11 is a cross-sectional view of a third alternative embodiment of the sensor of the fiber optic tracking system of FIG. 1.

Referring now to FIG. 11, a third alternative embodiment of the sensor 122 is shown from a cross-sectional end view. The sensor 122 includes a central wire 1102 with three indentations 1104 spaced equidistant around the circumference of the central wire 1102. Each indentation 1104 is substantially as deep as the diameter of a fiber 124-128, and has a contour that matches at least part of the surface of each fiber 124-128. A fiber (i.e., fiber A 124, fiber B 126, or fiber C 128) thereby fits within each indentation 1104 abutting the central wire 1102 as shown in FIG. 11. In various cases, the indentations 1104 are laser cut, mechanically milled (e.g., by computer-numerical-control machines), or chemically etched for high accuracy placement on the central wire 1102. In other cases, a material is extruded to form the central wire 1102 with the indentations 1104.

A low-friction sleeve 1106 surrounds the central wire 1102 and the fibers 124-128. An inner surface of the low-friction sleeve 1106 abuts the central wire 1102 around the circumference of the central wire 1102 except at the indentations 1104, where the low-friction sleeve 1106 confines the fibers 124-128 within the indentations 1104. The fibers 124-128 are thereby held at positions offset from a central axis or neutral line of the sensor 122, providing increased measurement resolution as described above. The low-friction sleeve 1106 also reduces friction, releases torsional stress (i.e., minimizes twisting), and provides thermal insulation for the sensor 122. Accordingly, the low-friction sleeve 908 is made of a low-friction, insulating material such as PTFE. An outer tube 1110 surrounds the low-friction sleeve 1106 to provide structure support and strength to the sensor 122. The central wire 1102 and the outer tube 910 are preferably made of nitinol or a material with similar characteristics.

Figure 12:
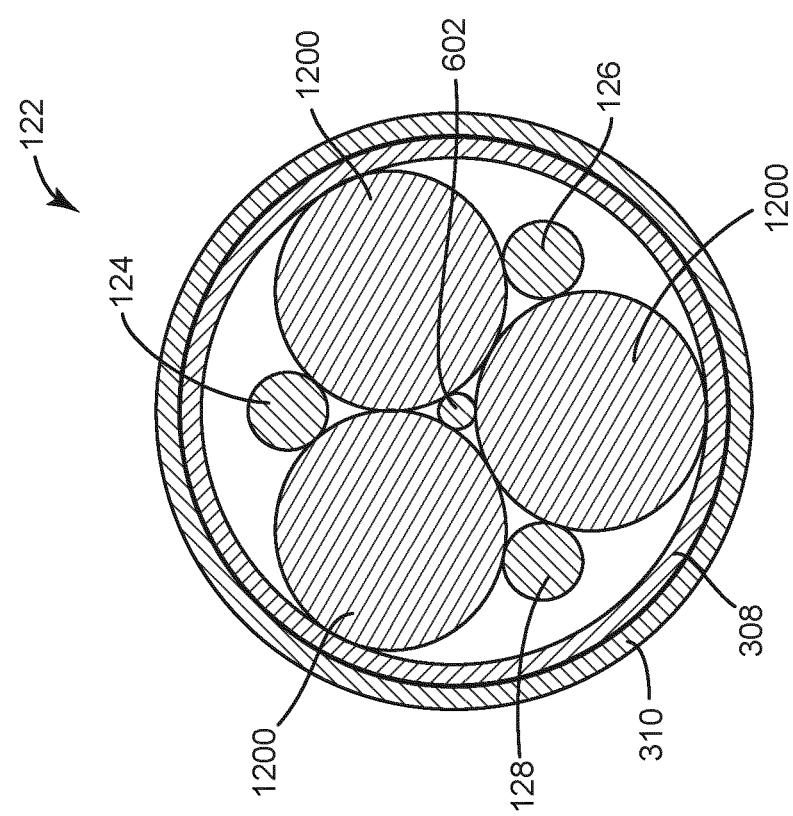
FIG. 12 is a cross-sectional view of a fourth alternative embodiment of the sensor of the fiber optic tracking system of FIG. 1.

Referring now to FIG. 12, a fourth alternative embodiment of the sensor 122 is shown from a cross-sectional end view. In the embodiment of FIG. 12, the sensor 122 includes three rods 1200 abutting one another and surrounded by the low-friction sleeve 308. The sleeve 308 is surrounded by the outer tube 310. The three rods 1200 each have a substantially equivalent diameter and are held in an arrangement such that the central axes of the rods 1200 define the vertices of a substantially equilateral triangle. The rods 1200 are formed from a shape-memory material, for example nitinol or another shape-memory alloy. The three fibers 124-128 are positioned around the rods 1200, with each fiber 124-128 abutting two of the rods 1200. The three fibers 124-128 are thereby also arranged in a substantially equilateral triangle. The three fibers 124-128 may be glued (adhered) to the rods 1200. The sensor 122 of FIG. 12 also includes a central optical fiber 602. The central optical fiber 602 is positioned between the rods 1200 at a central axis of the sensor 122 (i.e., a central axis of the low-friction sleeve 308 and the outer tube 310).

Figure 13:
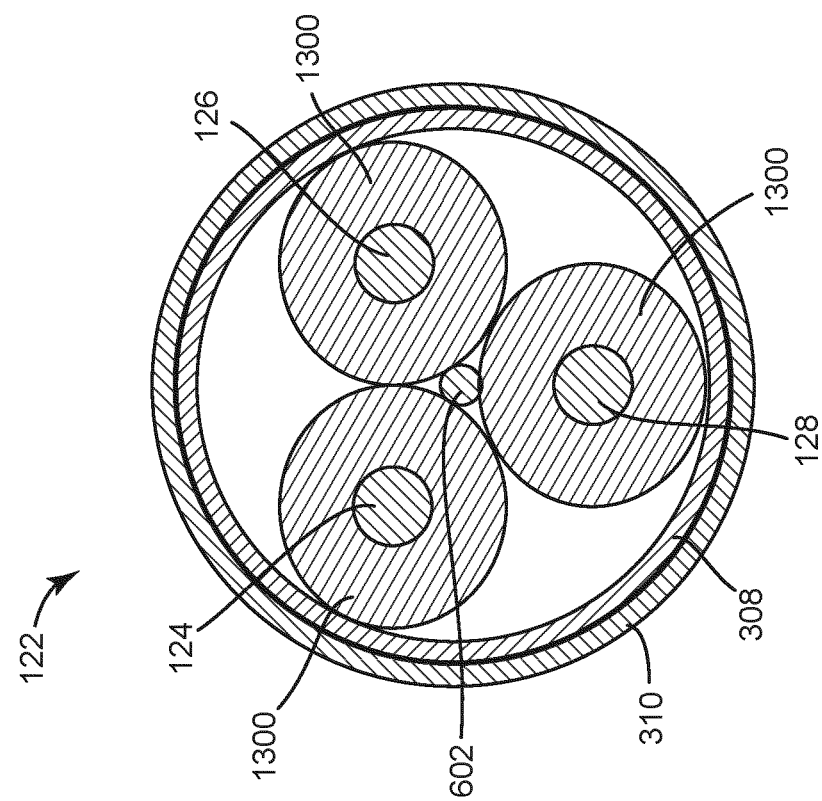
FIG. 13 is a cross-sectional view of a fifth alternative embodiment of the sensor of the fiber optic tracking system of FIG. 1.

Referring now to FIG. 13, a fifth alternative embodiment of the sensor 122 is shown from a cross-sectional end view. In the embodiment of FIG. 13, the sensor 122 includes three tubes 1300 abutting one another and surrounded by the by the low-friction sleeve 308. The sleeve 308 is surrounded by the outer tube 310. The three tubes 1300 have substantially identical diameters are arranged in a substantially equilateral triangle. The tubes 1300 may be formed (e.g., extruded) from a shape-memory material, for example nitinol or another shape-memory alloy. The optical fibers 124-128 are each positioned in one of the three tubes 1300. A central optical fiber 602 is positioned between the tubes 1300 at a central axis of the sensor 122 (i.e., a central axis of the low-friction sleeve 308 and the outer tube 310).

Referring now to FIG. 14, a sixth alternative embodiment of the sensor 122 is shown from a cross-sectional end view. As shown in FIG. 14, the sensor 122 includes a tube 1400 and three rods 1401. The tube 1400 includes a central passage 1402 in which a central optical fiber 602 is positioned. The tube 1400 also includes three fiber grooves 1404 and three rod grooves 1406. The three fiber grooves 1404 are configured to receive the three fibers 124-128. The three rod grooves 1406 are configured to receive the rods 1401. In the embodiment shown, the rods 1401 have a greater diameter than the fibers 124-128, and, accordingly, the rod grooves 1406 are larger than the fiber grooves 1404. A low-friction sleeve 308 surrounds the tube 1400, the fibers 124-128, and the rods 1401, holding the rods 1401 in the rod grooves 1406 and the fibers 124-128 in the fiber grooves 1404. An outer tube 310 surrounds the low-friction sleeve 308. The tube 1400 may be formed (e.g., extruded) from a shape-memory material, for example nitinol or another shape-memory alloy.

Referring now to FIG. 15, a seventh alternative embodiment of the sensor 122 is shown from a cross-sectional end view. As shown in FIG. 15, the sensor 122 includes a tube 1500 with seven channels, including a central channel 1502 and six peripheral channels 1504. The central channel 1502 extends through the tube 1500 along a central axis of the tube 1500. The peripheral channels 1504 extend through the tube 1500 proximate the periphery of the tube 1500, for example space equidistant from one another around the periphery of the tube 1500 (i.e., arranged in a regular hexagon arrangement). A central optical fiber 602 is positioned in the central channel 1502. The fibers 124-128 are each positioned in a peripheral channel 1504 (i.e., filling three of the six peripheral channels 1504) and three additional optical fibers 1506 are positioned in the remaining peripheral channels 1504. The additional optical fibers 1506 may have the same or similar properties as the fibers 124-128 as described above. Thus, in the embodiment of FIG. 15, the sensor 122 includes seven optical fibers that provide strain data to the fiber optic tracking system 106. The increased number of fibers may provide redundant measurements that may improve accuracy, sensor yield, and reliability. The sensor 122 of FIG. 15 also includes a low friction sleeve 308 that surrounds the tube 1500 and an outer tube 310 that surrounds the low-friction sleeve 308. The tube 1500 may be formed (e.g., extruded) from a shape-memory material, for example nitinol or another shape-memory alloy.

Figure 16:
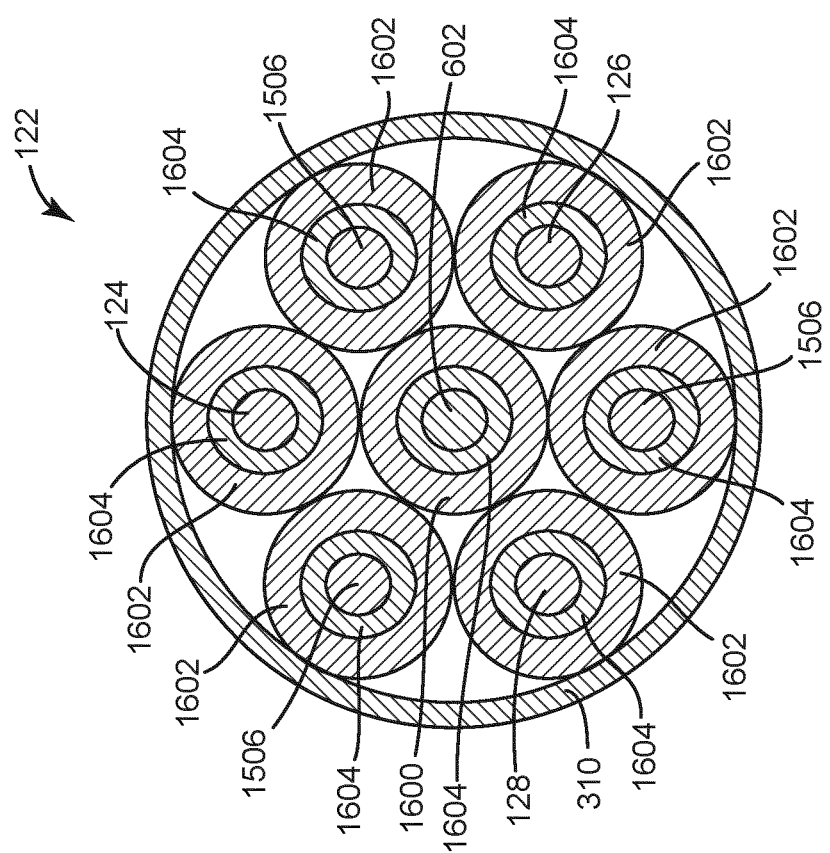
FIG. 16 is a cross-sectional view of an eight alternative embodiment of the sensor of the fiber optic tracking system of FIG. 1.

Referring now to FIG. 16, an eighth alternative embodiment of the sensor 122 is shown from a cross-sectional end view. As shown in FIG. 16, the sensor 122 includes seven tubes, including a central tube 1600 and six peripheral tubes 1602. The six peripheral tubes 1602 abut the central tube 1600 and surround the central tube 1600. Each of the six peripheral tubes 1602 is positioned such that the peripheral tube 1602 abuts the central tube 1600 and two of the five other peripheral tubes 1602. Each tube 1600-1602 houses a low-friction sleeve 1604, and each low-friction sleeve 1604 surrounds an optical fiber. A central optical fiber 602 is positioned in the central tube 1600. The fibers 124-126 are each positioned in a peripheral tube 1602 while three additional optical fibers 1506 are positioned in the remaining peripheral tubes 1602. Thus, in the embodiment of FIG. 16, the sensor 122 includes seven optical fibers that provide strain data to the fiber optic tracking system 106. An outer tube 310 surrounds the six peripheral tubes 1602 and holds the six peripheral tubes 1602 and the central tube 1600 together. The tubes 1600-1602 may be formed (e.g., extruded) from a shape-memory material, for example nitinol or another shape-memory alloy.

Figure 17:
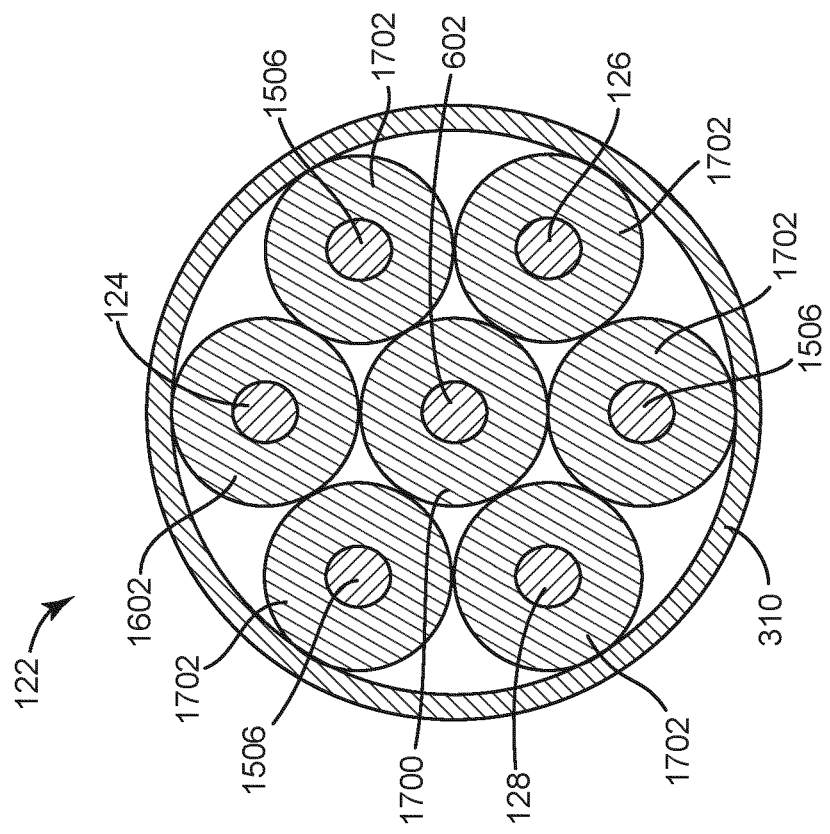
FIG. 17 is a cross-sectional view of a ninth alternative embodiment of the sensor of the fiber optic tracking system of FIG. 1.

Referring now to FIG. 17, a ninth alternative embodiment of the sensor 122 is shown from a cross-sectional end view. As shown in FIG. 17, the sensor 122 includes seven low-friction sleeves, including a central sleeve 1700 and six peripheral sleeves 1702. The six peripheral sleeves 1702 abut the central sleeve 1700. Each of the six peripheral sleeves 1702 is positioned such that the peripheral, low-friction sleeve 1702 abuts the central sleeve 1700 and two of the five other peripheral sleeves 1702. Each sleeve surrounds an optical fiber: the central sleeve 1700 houses a central optical fiber 602 and the peripheral sleeves 1702 house the fibers 124-128 and three additional fibers 1506. Thus, in the embodiment FIG. 17, the sensor 122 includes seven optical fibers that provide strain data to the fiber optic tracking system 106. An outer tube 310 surrounds the six peripheral sleeves 1702 and holds the peripheral sleeves 1702 and the central sleeve 1700 together.

Figure 18:
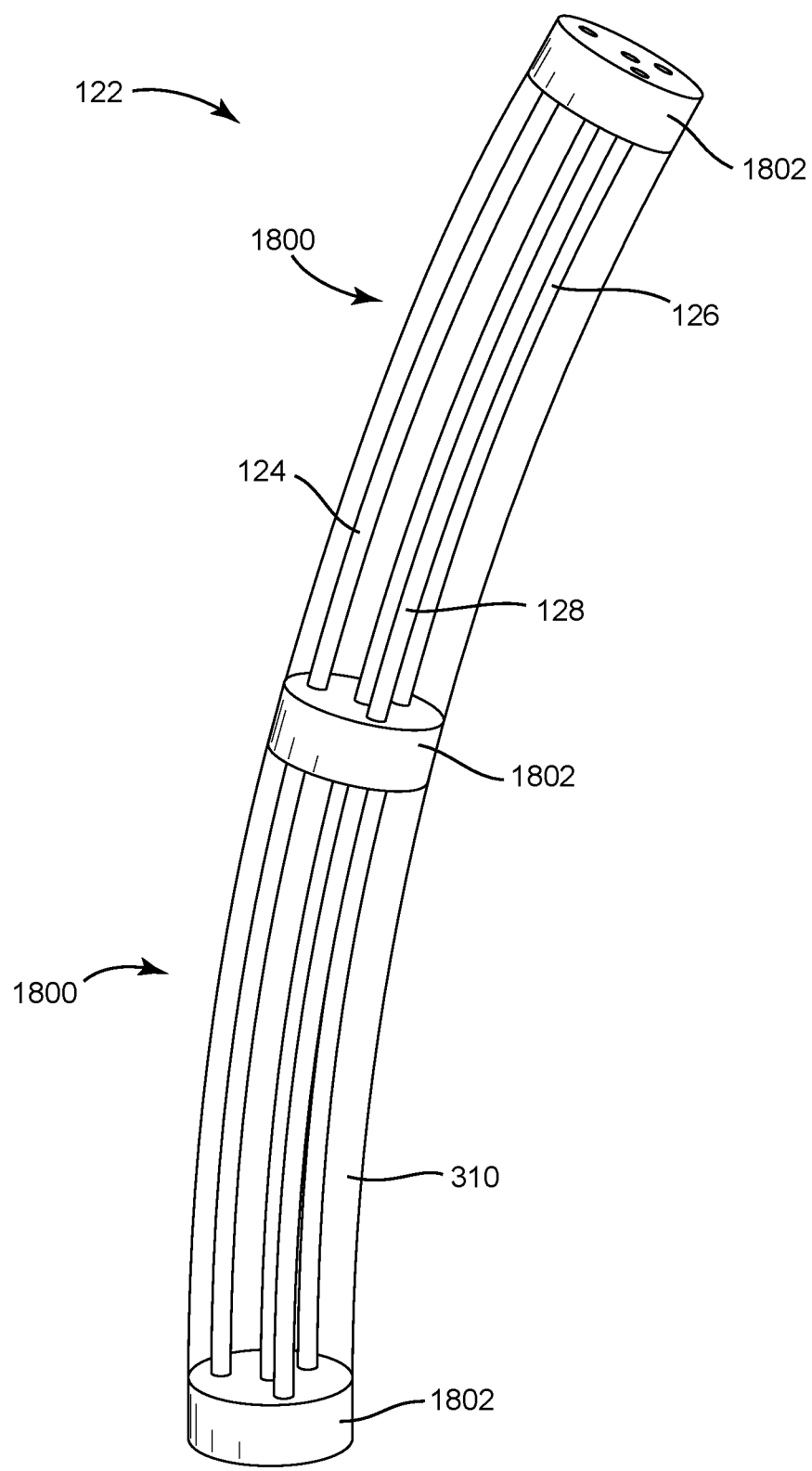
FIG. 18 is a perspective view of a tenth alternative embodiment of the sensor of the fiber optic tracking system of FIG. 1.

Referring now to FIG. 18, a perspective view of a tenth alternative embodiment of the sensor 122 is shown. As shown in FIG. 18, the sensor 122 includes flexible sections 1800 that extend between rigid disks 1802. The rigid disks 1802 bond multiple optical fibers (e.g., fibers 124-128) together in a known geometry at each rigid disk 1802. Between the rigid disks 1802, the flexible sections 1800 allow the sensor 122 to bend and flex. In some embodiments, the optical fibers 124-128 are not joined together in the flexible sections 1800 (i.e., only bound together at the rigid disks 1802), allowing the fibers 124-128 to bend independently. In some embodiments, a flexible shape-memory member, shown in FIG. 18 as outer tube 310, surrounds the fibers 124-128 and runs between the rigid disks 1802. Any number of flexible sections 1800 and rigid disks 1802 are possible.

In some embodiments, the flexible sections 1800 and the rigid disks 1802 may be substantially similar lengths. In such embodiments, the rigid disks 1802 may be described as rigid tubes, for example a substantially inflexible steel or aluminum tube. The fibers 124-128 may include FBGs 130 at the flexible sections 1800 with extended non-sensing sections positioned in the rigid sections/tubes. In some embodiments, the flexible sections 1800 are substantially shorter than the rigid sections, such that the flexible sections 1800 may be understood as joints between the rigid sections. The fibers 124-128 may include FBGs 130 at the joints. The strain data from the FBGs 130 at the joints may be used to determine an angle of each joint, which may then be combined with the known, fixed geometry of the rigid sections to determine the shape of the sensor 122. The present disclosure contemplates various combinations of any number of flexible sections/disks and rigid sections/disks of various lengths.

In the various embodiments of the sensor 122 shown and described herein, the sensor 122 includes various shape-memory members (e.g., first tube 304, second tube 306, outer tube 310, inner tube 604, outer tube 606, wires 616, central wire 902, slotted tube 904, outer tube 910, central wire 1102, outer tube 1110, rods 1200, tubes 1300, tube 1400, rods 1401, tube 1500, central tube 1600, peripheral tubes 1602, other features shown and/or described), various low-friction and thermally-insulating sleeves (e.g., sleeves 308, 908, 1106, 1604, 1702, other sleeves shown or described), and various optical fibers (e.g., fiber A 124, fiber B 126, fiber C 128, central fiber 602, additional fibers 1506, other fibers shown or described). Among other advantages, the shape-memory members minimize twisting of the fibers and help maintain the geometric relationship between fibers to minimize twist-based sensing errors and other errors. Among other advantages, the sleeves help to reduce, slow, evenly distribute, etc. thermal energy to reduce temperature-based sensing errors.

It should be understood that various additional combinations of such features are within the scope of the present disclosure. For example, although the example arrangements shown are symmetric, various other embodiments within the scope of the present disclosure may be asymmetric (e.g., more fibers located on one side of the sensor 122, shape-memory tubes or rods positioned asymmetrically, low-friction/thermal sleeves or sheaths positioned asymmetrically). As another example, although the example arrangements and elements have circular cross-sections, it should be understood that the sensor 122, the optical fibers, shape-memory members (e.g., tubes, rods), and low-friction/thermal sleeves may be various other regular and irregular shapes (e.g., triangular, rectangular, pentagonal, etc.).

The fiber optic tracking system 106 is thereby configured for use in tracking multiple anatomical features in a surgical procedure. More particularly, in some uses of the fiber optic tracking system 106 and the computer-assisted surgical system 100, base 202 is coupled to a first anatomical feature, first bone clamp 204 is coupled to a second anatomical feature, and second bone clamp 206 is coupled to a third anatomical feature. The sensor 122 is then coupled to the base 202, the first bone clamp 204, and the second bone clamp 206. The sensor 122 may be similarly coupled to one or more additional anatomical features, surgical tools, objects, probes, robotic devices, etc. as required for a particular procedure, including a combination of different types of objects For example, the sensor 122 may be coupled to both an anatomical feature and a surgical tool (e.g., cutting tool) or to both an anatomical feature and a robotic device (e.g., robotic arm, handheld robotic device) to facilitate tracking of the surgical tool or robotic device relative to the anatomical feature.

The interrogator 120 then transmits light into and receives reflections from the sensor 122 to generate strain data. The strain data is received by the tracking circuit 112, which uses the strain data to determine the shape of the sensor 122. The sensor 122 may then be registered using the optical tracking system 104. That is, the relationship between fiducial member 215 and sensor clamp 214 may be determined using the optical tracking system 104 and an optical probe, and then that relationship may be used to register the overall shape of the sensor 122 to a coordinate system used by the optical tracking system 104. Various other points along the sensor 122 may also be included in the registration process to establish the geometric relationship between various points on the sensor 122 and various anatomical features (e.g., by touching a registration probe to one or more points along the sensor 122 and to the related anatomic features). For example, in the example of FIG. 2A, the registration probe may be touched to the sensor 122 at the sensor clamps 220, 230 as well as to the positions on the patient's bones where the first bone clamp 204 and the second bone clamp 206 engage the bones. The shape of the sensor 122 may thereby be mapped to positions of the anatomical features (or other relevant objects).

The positions of the third anatomical features or other objects can then be determined based on the shape of the sensor 122, and updated as the shape of the sensor 122 changes. The positions of the anatomical features or other objects may be presented on a visual display to a healthcare provider, used in controlling an automated or autonomous robotic device, and/or used in generating force feedback for a user of a surgical tool, for example as part of a haptic device.

Various exemplary embodiments are described herein. Reference is made to these examples in a non-limiting sense. They are provided to illustrate more broadly applicable aspects of the invention. Various changes may be made to the embodiments described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure. In addition, where a range of values is provided, it is understood that every intervening value, between the upper and lower limit of that range and any other stated or intervening value in that stated range, is encompassed within the invention.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The present disclosure includes methods that may be performed using the subject devices. The methods may include the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

What is claimed is:

1. A fiber optic tracking sensor, comprising:
   an outer tube;
   a plurality of optical fibers within the outer tube and comprising a central optical fiber and a plurality of additional optical fibers; and
   one or more structural members within the outer tube and configured to provide a spacing between the plurality of optical fibers such that the central optical fiber is positioned along a central longitudinal axis of the outer tube and the plurality of additional optical fibers are spaced apart from one another and from the central optical fiber;
   wherein the one or more structural members comprise an inner tube, the inner tube separating the central optical fiber from the plurality of additional optical fibers.

2. The fiber optic tracking sensor of claim 1, wherein the plurality of optical fibers comprises a plurality of fiber Bragg gratings.

3. The fiber optic tracking sensor of claim 1, wherein the plurality of additional optical fibers are positioned in channels or grooves between the outer tube and the inner tube.

4. The fiber optic tracking sensor of claim 3, wherein the one or more structural members further comprise wires positioned in the channels or grooves.

5. The fiber optic tracking sensor of claim 1, wherein the plurality of additional optical fibers are positioned in channels through the inner tube.

6. The fiber optic tracking sensor of claim 1, wherein the one or more structural members comprise a plurality of sleeves comprising a first sleeve surrounding a first optical fiber of the plurality of optical fibers, a second sleeve surrounding a second fiber of the plurality of optical fibers, and a third sleeve surrounding a third optical fiber of the plurality of optical fibers.

7. A fiber optic tracking sensor, comprising:
an outer tube;
a plurality of optical fibers within the outer tube; and
a plurality of abutting tubes or rods within the outer tube and configured to provide a spacing between the plurality of optical fibers such that the plurality of optical fibers are spaced apart from one another, wherein a central optical fiber is positioned in a central space between the abutting tubes or rods, the abutting tubes or rods in direct contact with one another.

8. The fiber optic tracking system of claim 7, wherein the plurality of abutting tubes or rods comprise a first tube surrounding a first fiber of the optical fibers and a second tube surrounding a second fiber of the optical fibers.

9. The fiber optic tracking system of claim 7, wherein the plurality of optical fibers are positioned between the outer tube and the plurality of abutting tubes or rods.

10. A fiber optic tracking sensor comprising:
a plurality of tubes comprising a first tube, a second tube, and a third tube;
a first optical fiber surround by the first tube, a second optical fiber surrounded by the second tube, and a third optical fiber surround by the third tube;
wherein the first tube abuts the second tube and the third tube;
wherein the first optical fiber, the second optical fiber, and the third optical fiber are arranged in a spaced apart relationship provided by thicknesses of the first tube, the second tube, and the third tube;
wherein the fiber optic tracking sensor further comprises a sleeve between the first optical fiber and the first tube, the sleeve surrounded by the first tube.

11. The fiber optic tracking sensor of claim 10, wherein the first optical fiber, the second optical fiber, and the third optical fiber are offset from a central longitudinal axis of the fiber optic tracking sensor.

12. The fiber optic tracking sensor of claim 10, wherein the second tube abuts the third tube.

13. The fiber optic tracking sensor of claim 12, further comprising a fourth optical fiber positioned in a central gap between the first tube, the second tube, and the third tube.

14. The fiber optic tracking sensor of claim 10, further comprising an outer tube surrounding the first tube, the second tube, and the third tube.

15. A fiber optic tracking system, comprising:
an outer tube;
a first member within the outer tube and positioned along a central longitudinal axis of the outer tube, wherein the first member is a wire;
one or more additional members between the first member and the outer tube, the one or more additional members comprising a slotted tube and a sleeve; and
a plurality of optical fibers positioned in slots of the slotted tube, wherein the sleeve is between the outer tube and the wire.

16. The fiber optic tracking system of claim 15, wherein the slotted tube is between the sleeve and the wire.

* * * * *